US009137453B2

(12) United States Patent
Tanaka et al.

(10) Patent No.: US 9,137,453 B2
(45) Date of Patent: Sep. 15, 2015

(54) CONTROL APPARATUS AND IMAGING SYSTEM

(71) Applicant: OLYMPUS MEDICAL SYSTEMS CORP., Tokyo (JP)

(72) Inventors: Satoshi Tanaka, Hino (JP); Kotaro Ogasawara, Tokyo (JP); Tomoya Takahashi, Hachioji (JP); Yusuke Yabe, Sagamihara (JP); Susumu Hashimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/163,446

(22) Filed: Jan. 24, 2014

(65) Prior Publication Data

US 2014/0198249 A1    Jul. 17, 2014

Related U.S. Application Data

(63) Continuation of application No. PCT/JP2013/064931, filed on May 29, 2013.

(30) Foreign Application Priority Data

Jul. 24, 2012    (JP) .................................. 2012-164168

(51) Int. Cl.
  *H04N 5/235*    (2006.01)
  *G02B 23/24*    (2006.01)
  (Continued)

(52) U.S. Cl.
  CPC .......... *H04N 5/2354* (2013.01); *A61B 1/00006* (2013.01); *A61B 1/045* (2013.01); *A61B 1/0661* (2013.01); *G02B 23/2476* (2013.01); *H04N 5/2256* (2013.01); *H04N 5/3532* (2013.01)

(58) Field of Classification Search
  CPC . H04N 5/2354; H04N 5/2256; H04N 5/3532; G02B 23/2476; A61B 1/045; A61B 1/00006; A61B 1/0661
  USPC ........... 348/65, 68, 69, 70, 71, 72, 73, 74, 77, 348/216.1, 217.1, 220.1, 221.1, 222.1, 348/229.1, 230.1, 241, 255, 294, 295, 296, 348/362, 363, 364, 365, 366, 367, 370, 371
  See application file for complete search history.

(56) References Cited

U.S. PATENT DOCUMENTS 7,884,856 B2    2/2011  Nikura
8,550,990 B2 *  10/2013 Seto et al. ..................... 600/180
(Continued)

FOREIGN PATENT DOCUMENTS

JP    2007-243680 A    9/2007
JP    2008-104614 A    5/2008
(Continued)

OTHER PUBLICATIONS

International Search Report dated Jun. 25, 2013 from related International Application No. PCT/JP2013/064931, together with an English language translation.

(Continued)

*Primary Examiner* — Twyler Haskins
*Assistant Examiner* — Peter Chon
(74) *Attorney, Agent, or Firm* — Scully, Scott, Murphy & Presser, PC

(57) ABSTRACT

A control apparatus includes a control unit configured to control a cycle from a first irradiation start timing to a second irradiation start timing to be shorter than a cycle of each of first and second picture periods. The first irradiation start timing is a timing at which a light source device starts radiating pulsed illumination light in the first picture period in which an image pickup device performs reading. The second irradiation start timing is a timing at which the light source device starts radiating the illumination light in the second picture period succeeding the first picture period and having the same cycle as the first picture period.

6 Claims, 20 Drawing Sheets

(51) Int. Cl.
*A61B 1/045* (2006.01)
*A61B 1/00* (2006.01)
*A61B 1/06* (2006.01)
*H04N 5/225* (2006.01)
*H04N 5/353* (2011.01)

(56) References Cited

U.S. PATENT DOCUMENTS

| 8,643,710 | B2* | 2/2014 | Ono et al. | 348/68 |
| 2011/0001859 | A1* | 1/2011 | Matsuura et al. | 348/296 |

FOREIGN PATENT DOCUMENTS

| JP | 2009-165711 A | | 7/2009 |
| JP | 2009165711 A | * | 7/2009 |
| JP | 2012-19429 A | | 1/2012 |
| JP | 2012019429 A | * | 1/2012 |

OTHER PUBLICATIONS

Notice of Rejection dated Mar. 25, 2014 from related Japanese Application No. 2014-501766, together with an English language translation.

* cited by examiner

CONTROL APPARATUS AND IMAGING SYSTEM

CROSS REFERENCES TO RELATED APPLICATIONS

This application is a continuation of PCT international application Ser. No. PCT/JP2013/064931 filed on May 29, 2013 which designates the United States, incorporated herein by reference, and which claims the benefit of priority from Japanese Patent Application No. 2012-164168, filed on Jul. 24, 2012, incorporated herein by reference.

BACKGROUND OF THE INVENTION

1. Field of the Invention

The present invention relates to a control apparatus which collectively controls an image pickup device and a light source device, and to an imaging system including the image pickup device and the light source device.

2. Description of the Related Art

A conventional CMOS (Complementary Metal Oxide Semiconductor) image sensor often applies a rolling shutter method in which exposure and readout timings change in each horizontal line. The rolling shutter method applies a different exposure timing for each horizontal line in a single picture period, where uneven brightness generated in an image has been a problem when imaging while irradiating with illumination light for only a very short period of time, for example.

When a high-brightness area generated by illumination of the illumination light stretches over two picture periods, an image of the high-brightness area in the picture period being imaged first replaces and corrects a corresponding area in the picture period being imaged later by a known technique, as a technique to eliminate the uneven brightness generated in the CMOS image sensor applying the rolling shutter method (refer to Japanese Laid-open Patent Application Publication No. 2012-19429, for example).

FIG. 19 is a diagram illustrating an example of a relationship between a timing at which pulsed illumination light is emitted and each horizontal line being read in the picture period according to a conventional imaging system. For the convenience of description, it is assumed in FIG. 19 that the number of horizontal lines of an imaging signal equals 18 and that the horizontal lines are read in sequence from the top. In FIG. 19, "VD" indicates a timing at which a vertical synchronizing signal is generated while "HD" indicates a timing at which a horizontal synchronizing signal is generated. Moreover, a horizontal axis "t" in FIG. 19 indicates a time axis.

A readout period In (n=1 to 18) of a frame I (where I is a natural number) indicates a readout period of an n-th horizontal line from the top in the frame I. Similar to the readout period In, each of a readout period Jn of a frame J (=I+1) and a readout period Kn of a frame K (=I+2) indicates a readout period of an n-th horizontal line from the top in the frames J and K, respectively.

In the frame I illustrated in FIG. 19, a pulse is illuminated for the duration equivalent to three readout periods from a readout period I8 as a starting point. Accordingly, the exposure amount in the image corresponding to the imaging signal of each horizontal line being read in the frame I varies according to the relationship between a pulse illuminated period $T_{9I}$ and the readout period in terms of a temporal position. Specifically, the exposure amount in an image corresponding to an imaging signal being read in each of readout periods I1 to I8 all equals zero. Note that the pulse is not illuminated in a frame H (=I−1) in this example. On the other hand, the exposure amount in an image corresponding to an imaging signal being read in each of readout periods I11 to I18 is equivalent to the amount when the pulse is illuminated for the pulse illuminated period $T_{9I}$. The exposure amount in an image corresponding to an imaging signal being read in a readout period I9 is equivalent to the amount when the pulse is illuminated for a single readout period. The exposure amount in an image corresponding to an imaging signal being read in a readout period I10 is equivalent to the amount when the pulse is illuminated for two readout periods.

An image corresponding to an imaging signal being read in a specified period is hereinafter referred to as an image read in a specified period. Moreover, exposure amount equivalent to the amount when the pulse is illuminated for the specified period is referred to as exposure amount corresponding to the specified period.

Now, an image read in the frame J will be described. The exposure amount in an image being read in each of readout periods J1 to J7 in the frame J corresponds to the pulse illuminated period $T_{9I}$. On the other hand, the exposure amount in an image being read in each of readout periods J10 to J18 all equals zero. The exposure amount in an image being read in a readout period J8 corresponds to a single readout period. The exposure amount in an image being read in a readout period J9 corresponds to two readout periods.

FIG. 20 is a diagram schematically illustrating an image being read out in the case illustrated in FIG. 19. Images 9I, 9J, and 9IJ in FIG. 20 schematically illustrate the difference in the exposure amount described above by different patterns. This is common to all images illustrated in other drawings.

FIG. 20 illustrates a case where the images 9I and 9J both have uneven brightness. What is performed in the conventional technique in order to reduce the uneven brightness in the image 9J is that an image read in the readout periods J10 to J18 in the frame 9J is replaced by an image read in the readout periods I10 to I18 in the image 9I to create a corrected image 9IJ is uniform excluding the area corresponding to the three horizontal lines in the readout periods J8, J9, and I10, whereby the uneven brightness is reduced compared to the uncorrected image 9J.

SUMMARY OF THE INVENTION

A control apparatus according to one aspect of the invention is communicably connected to each of an image pickup device and a light source device and collectively controls an operation of the image pickup device and the light source device. The control apparatus includes a control unit configured to control a cycle from a first irradiation start timing to a second irradiation start timing to be shorter than a cycle of each of first and second picture periods, the first irradiation start timing being a timing at which the light source device starts radiating pulsed illumination light in the first picture period in which the image pickup device performs reading, and the second irradiation start timing being a timing at which the light source device starts radiating the illumination light in the second picture period succeeding the first picture period and having the same cycle as the first picture period. The image pickup device is configured to read out an imaging signal generated by a plurality of pixels for each horizontal line, the plurality of pixels being arranged in two dimensions to generate the imaging signal by performing photoelectric conversion on an optical image of a subject. The light source device includes a light source configured to generate the pulsed illumination light with which the subject is irradiated at a timing overlapping with a readout period that is a period in which the imaging signal is read out for each horizontal line from the image pickup device.

An imaging system according to one aspect of the invention includes: an image pickup device in which a plurality of pixels are arranged in two dimensions to generate an imaging signal by performing photoelectric conversion on an optical image of a subject and which is configured to read out the imaging signal generated by the plurality of pixels for each horizontal line; a light source device which includes a light source configured to generate pulsed illumination light with which the subject is irradiated at a timing overlapping with a readout period that is a period in which the imaging signal is read out for the each horizontal line from the image pickup device; and a control unit which is communicably connected to each of the image pickup device and the light source device and configured to control a cycle from a first irradiation start timing to a second irradiation start timing to be shorter than a cycle of each of first and second picture periods, the first irradiation start timing being a timing at which the light source device starts radiating the illumination light in the first picture period in which the image pickup device performs reading, and the second irradiation start timing being a timing at which the light source device starts radiating the illumination light in the second picture period succeeding the first picture period and having the same cycle as the first picture period.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Modes for carrying out the present invention (hereinafter referred to as "embodiments") will be described below with reference to the attached drawings. Note that the drawings referenced in the following description are schematic illustrations and may have a different dimension or scale when the same object is illustrated in a different drawing.

First Embodiment

Figure 1:
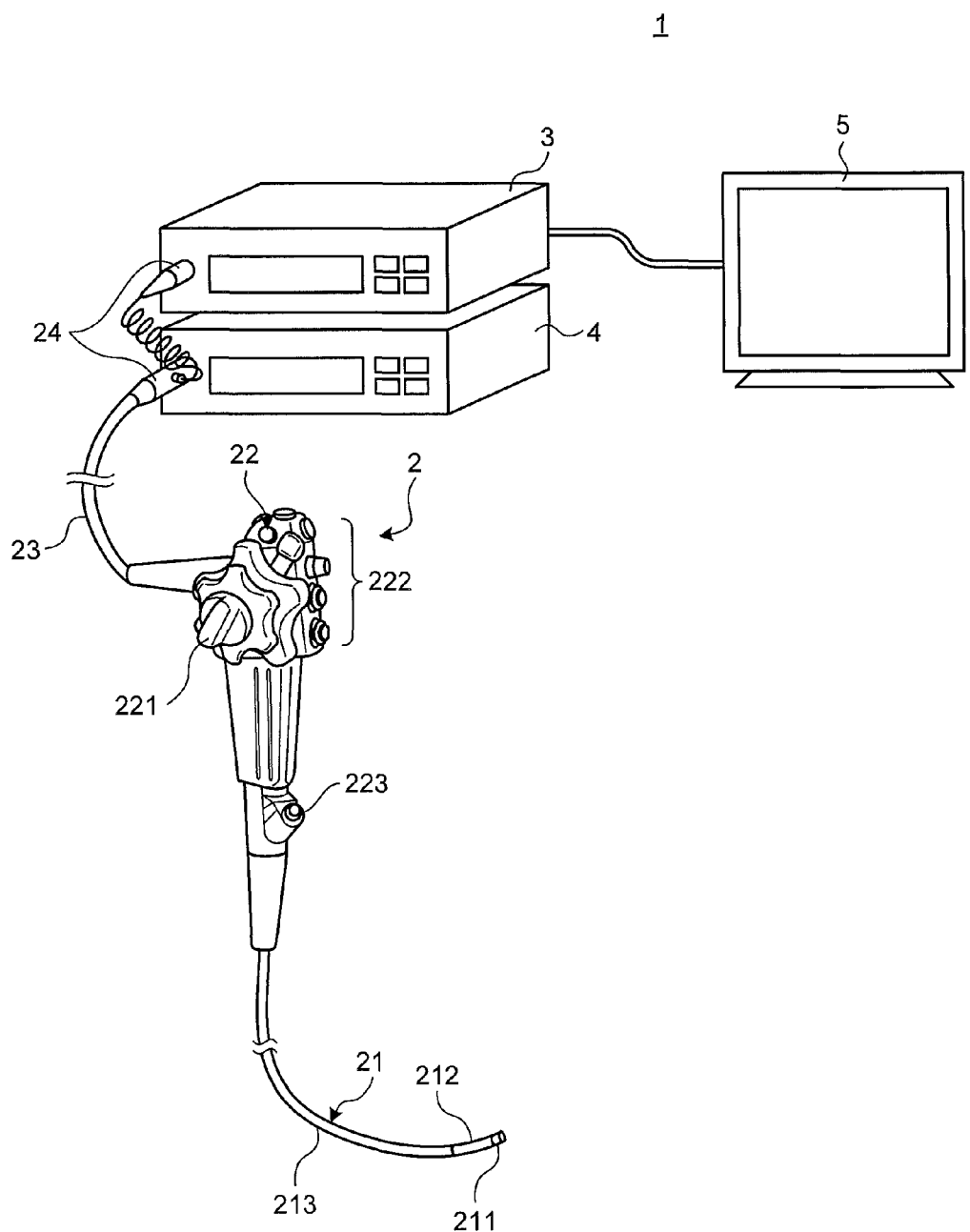
FIG. 1 is a diagram illustrating a schematic configuration of an endoscope system that is an imaging system according to a first embodiment of the present invention.
Figure 2:
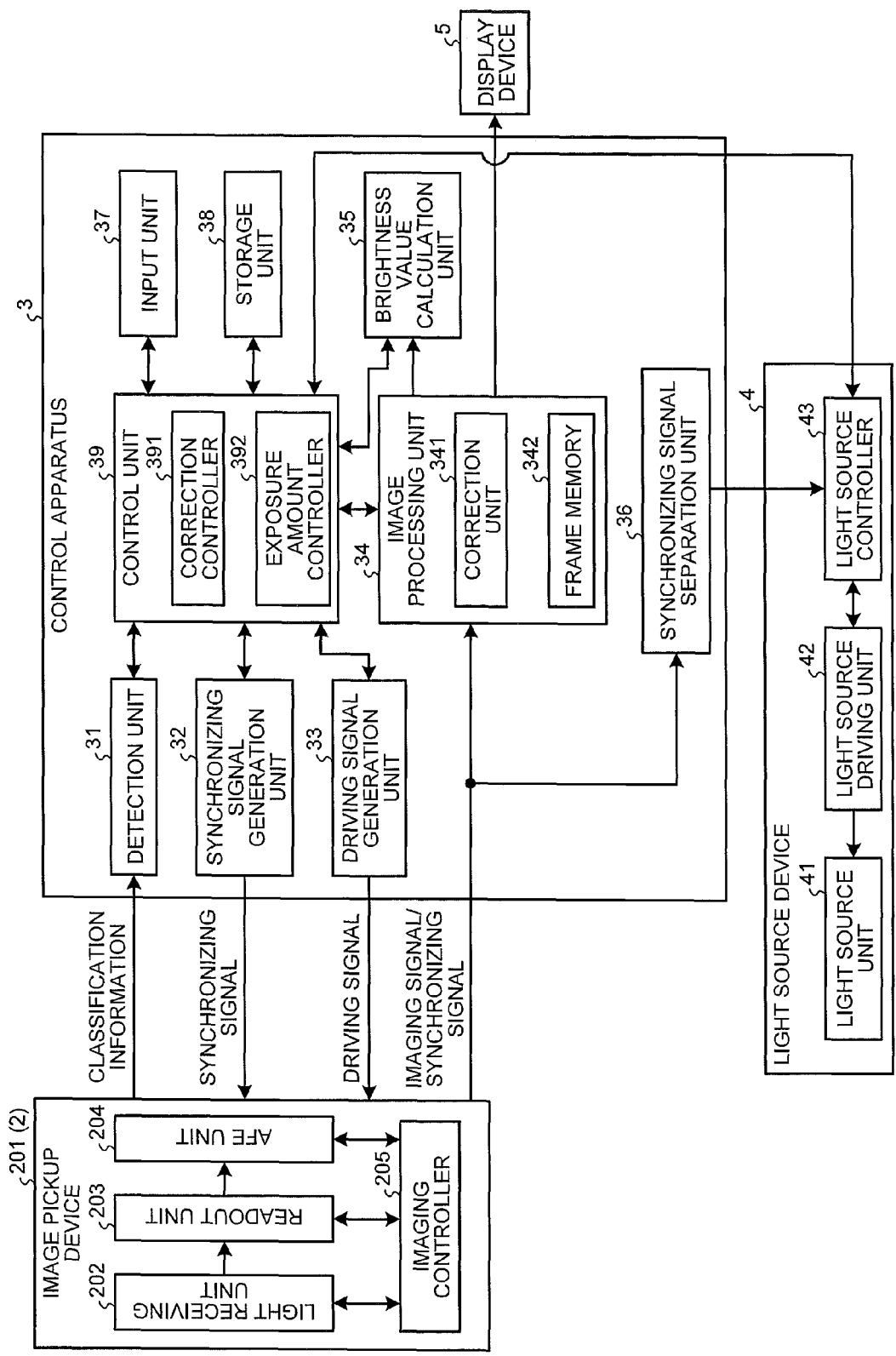
FIG. 2 is a block diagram illustrating a functional configuration of a principal part of the endoscope system that is the imaging system according to the first embodiment of the present invention.

FIG. 1 is a diagram illustrating a schematic configuration of an endoscope system that is an imaging system according to first embodiment of the present invention. FIG. 2 is a block diagram illustrating a functional configuration of a principal part of the endoscope system that is the imaging system according to the first embodiment of the present invention. An endoscope system 1 illustrated in FIGS. 1 and 2 includes an endoscope 2, a control apparatus 3, a light source device 4, and a display device 5. The endoscope 2 captures an in-vivo image of a subject by inserting a distal end portion of the endoscope into the subject. The control apparatus 3 performs specified image processing on the in-vivo image being imaged by the endoscope 2 as well as collectively controls the overall operation of the endoscope system 1. The light source device 4 produces illumination light that is emitted from the distal end of the endoscope 2. The display device 5 displays the in-vivo image onto which the image processing is performed by the control apparatus 3.

The endoscope 2 includes an insertion unit 21, an operating unit 22, a universal cord 23, and a connector unit 24. The insertion unit 21 is in an elongated shape having flexibility. The operating unit 22 is connected to a proximal end side of the insertion unit 21 and accepts input of various operation signals. The universal cord 23 extends from the operating unit 22 in a direction different from the direction into which the insertion unit 21 extends, and includes various cables built in to be connected to the control apparatus 3 and the light source device 4. The connector unit 24 is provided at a proximal end portion of the universal cord 23 detachably from the control apparatus 3 and the light source device 4, and transmits/receives an electric signal and an optical signal between the control apparatus 3 and the light source device 4.

The insertion unit 21 includes a distal end portion 211 which has an image pickup device 201 built in, a bent portion 212 which is formed of a plurality of bending pieces and can be bent freely, and a long flexible tube portion 213 which has flexibility and is connected to a proximal end side of the bent portion 212.

The distal end portion 211 includes a light guide forming a light guide path of the light emitted from the light source device 4, an illumination lens provided at a distal end of the light guide, and a condensing optical system.

The image pickup device 201 is configured such that pixels which generate a signal by receiving light and performing photoelectric conversion are arranged in two dimensions, receives the light, and performs the photoelectric conversion to generate an electric signal. The image pickup device 201 includes a light receiving unit 202, a readout unit 203, an analog front end unit 204 (hereinafter referred to as an "AFE unit 204"), and an imaging controller 205. In the light receiving unit 202, a plurality of pixels is arranged two-dimensionally for generating a signal by performing the photoelectric conversion on an optical image of a subject. The readout unit 203 reads out as image information an imaging signal generated by a pixel that is arbitrarily set as a pixel to be read from among the plurality of pixels in the light receiving unit 202. The AFE unit 204 performs denoising and A/D conversion on the imaging signal being output by the readout unit 203. The imaging controller 205 controls the operation of the image pickup device 201. The image pickup device 201 is provided at a position where the optical system forms an image.

The image pickup device 201 is a CMOS image sensor applying a rolling shutter method and sequentially reads out an accumulated electric charge one horizontal line at a time. This causes a time difference in the readout timing between the horizontal line that is read first by the readout unit 203 and the horizontal line that is read last by the readout unit.

The pixel configuring the light receiving unit 202 includes a photodiode which accumulates the electric charge according to the amount of light, and an amplifier which amplifies the electric charge accumulated by the photodiode. Each pixel is provided with a color filter on a light receiving surface of the light receiving unit 202.

The AFE unit 204 includes a noise reduction circuit which reduces a noise component included in an analog imaging signal by using a correlated double sampling method or the like, an AGC (Automatic Gain Control) circuit which maintains a fixed output level by adjusting an amplification factor (gain) of an electric signal, and an A/D conversion circuit which performs A/D conversion on the imaging signal as the image information that is output through the AGC circuit.

The imaging controller 205 controls various operation of the distal end portion 211 on the basis of setting data received from the control apparatus 3. The imaging controller 205 is formed of a CPU (Central Processing Unit) and a register which records various programs, for example.

The operating unit 22 includes a bending knob 221 which bends the bent portion 212 in a vertical direction and a horizontal direction, and a plurality of switches 222 that is an operation inputting unit which inputs an operation instruction signal for peripheral equipment including the control apparatus 3 and the light source device 4. The operating unit 22 is provided with a treatment tool insertion unit 223 into which a treatment tool is inserted from outside.

The universal cord 23 incorporates therein at least a light guide and a cable assembly formed of one or a plurality of signal lines bundled together.

The configuration of the control apparatus 3 will now be described. The control apparatus 3 includes a detection unit 31, a synchronizing signal generation unit 32, a driving signal generation unit 33, an image processing unit 34, a brightness value calculation unit 35, a synchronizing signal separation unit 36, an input unit 37, a storage unit 38, and a control unit 39. The detection unit 31 detects classification information transmitted from the image pickup device 201. The synchronizing signal generation unit 32 generates a synchronizing signal that provides an exposure timing and a readout timing of each horizontal line for the image pickup device 201 and outputs the signal to the image pickup device 201. The driving signal generation unit 33 generates a driving signal that drives the image pickup device 201 and transmits the signal to the image pickup device 201. The image processing unit 34 performs specified image processing on the imaging signal received from the image pickup device 201. The brightness value calculation unit 35 calculates a brightness value of the image that is processed by the image processing unit 34. The synchronizing signal separation unit 36 separates the synchronizing signal from the imaging signal, the synchronizing signal being superimposed onto the imaging signal received from the image pickup device 201. The input unit 37 accepts input of various signals such as an operation instruction signal which instructs an operation of the endoscope system 1. The storage unit 38 stores various pieces of information pertaining at least to the control apparatus 3. The control unit 39 performs overall control on the operation of the control apparatus 3.

The image processing unit 34 includes a correction unit 341 which corrects uneven brightness in the image by replacing images between two frames (picture periods) imaged in sequence, and a frame memory 342 which stores at least image data corresponding to the latest frame being read by the readout unit 203. The correction unit 341 may have a function to perform digital processing that amplifies or attenuates the imaging signal of a part having the exposure amount (brightness) different from another horizontal line.

The brightness value calculation unit 35 calculates the brightness value of the image corrected by the correction unit 341.

The storage unit 38 records data including various programs provided to operate the endoscope system 1 and various parameters required in the operation of the endoscope system 1. The storage unit 38 further records identification information of the control apparatus 3. Here, the identification information includes inherent information (ID), an age, specification information, a transmission method, a transmission rate, and the like of the control apparatus 3. The storage unit 38 is realized by employing a semiconductor memory such as a flash memory or a DRAM (Dynamic Random Access Memory).

The control unit 39 includes a correction controller 391 and an exposure amount controller 392. The correction controller 391 controls correction performed by the correction unit 341. The exposure amount controller 392 performs control to set an electronic shutter of the image pickup device 201 as well as the amount of illumination light provided and a pulse illumination timing by the light source device 4 on the basis of the calculation result by the brightness value calculation unit 35 and a target brightness value. The control unit 39 is formed of a CPU and the like.

The exposure amount controller 392 performs control such that successive two frames (first and second picture periods) are irradiated with the illumination light by the light source device 4 at different irradiation timings.

The configuration of the light source device 4 will now be described. The light source device 4 includes a light source unit 41 which produces the illumination light radiated outside from the distal end portion 211 of the endoscope 2, a light source driving unit 42 which drives the light source unit 41, and a light source controller 43 which controls the operation of the light source device 4 on the basis of a signal transmitted from the exposure amount controller 392 of the control apparatus 3.

The light source unit 41 is formed of a white LED. Pulsed white light illuminated by the light source unit 41 reaches the distal end portion 211 of the insertion unit 21 through the connector unit 24 and the universal cord 23 and serves as the illumination light that is radiated from the distal end portion 211 toward a subject. Note that a non-white LED or laser may be applied as the light source unit 41 as well.

The configuration of the display device 5 will now be described. The display device 5 is connected to the control apparatus 3 to be able to communicate therewith through an image cable. The display device 5 displays an image generated by the control apparatus 3 by receiving the image from the control apparatus 3. Such display device 5 is formed of a liquid crystal or organic EL (Electro Luminescence).

Next, there will be described the overview of a process performed when the endoscope system 1 including the aforementioned configuration shoots a moving image. The exposure amount controller 392 sets a cycle of a timing at which the pulse starts to be illuminated by the light source device 4 to be shorter than a cycle of a single frame by the amount of time equivalent to a readout period of a single horizontal line. Under control of the correction controller 391, the correction unit 341 generates a corrected image by replacing an area of an image being read in the latest frame (the second picture period) by the readout unit 203 with a recorded image, the area corresponding to the recorded image that is read after a pulse illuminated period in a preceding frame (the first picture period) and recorded in the frame memory 342.

The overview of a correction process performed by the correction unit 341 will be described below by cases where:

(1-1) the pulse illuminated period gradually increases; (1-2) the pulse illuminated period gradually decreases; and (1-3) the pulse illuminated period is fixed.

(1-1) When the Pulse Illuminated Period Gradually Increases

Figure 3:
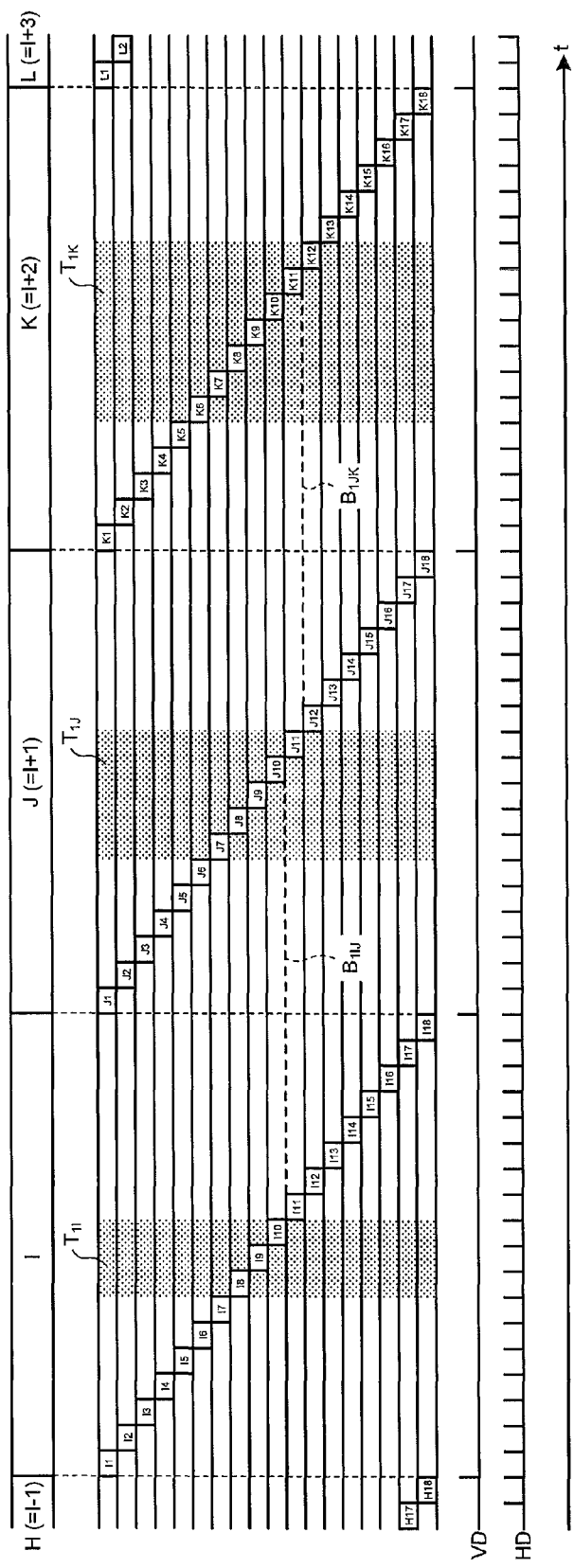
FIG. 3 is a diagram schematically illustrating the overview of an image acquisition method implemented, when a pulse illuminated period gradually increases, by the endoscope system that is the imaging system according to the first embodiment of the present invention.

FIG. 3 is a diagram schematically illustrating the overview of an image acquisition method implemented by the endoscope system 1 when the pulse illuminated period gradually increases. In order to simplify the description, it is hereinafter assumed that the number of horizontal lines of the imaging signal equals 18 and that the readout unit 203 reads the horizontal lines sequentially from the top.

A broken line $B_{1IJ}$ illustrated in FIG. 3 indicates an image replacement boundary along which a part of an image read by the readout unit 203 in a frame J is replaced by a corresponding area of an image read by the readout unit 203 in a frame I. Likewise, a broken line $B_{1JK}$ indicates an image replacement boundary along which a part of an image read by the readout unit 203 in a frame K is replaced by a corresponding area of an image read by the readout unit 203 in the frame J.

In the case illustrated in FIG. 3, the exposure amount controller 392 sets a pulse illumination start timing in the frame I to a starting point of a readout period I8, and sets a cycle from the starting point to a next pulse illumination start timing to be shorter than the cycle of the frame I by one readout period. Accordingly, the next pulse illumination start timing corresponds to a starting point of a readout period J7 in the frame J. Likewise, the exposure amount controller 392 sets a pulse illumination start timing that comes after the starting point of the readout period J7 to a starting point of a readout period K6 in the frame K. Note that it is assumed in the following description that, in FIG. 3, the pulse is illuminated not up to a frame H (=I−1) but starting from the frame I.

The duration of a pulse illuminated period $T_{1I}$ in the frame I in FIG. 3 equals the duration of the readout period corresponding to three horizontal lines (three readout periods). The duration of a pulse illuminated period $T_{1J}$ in the frame J equals the duration of five readout periods. Moreover, the duration of a pulse illuminated period $T_{1K}$ in the frame K equals the duration of seven readout periods. It is needless to say that such setting of the pulse illuminated period is merely provided as an example.

Figure 4:
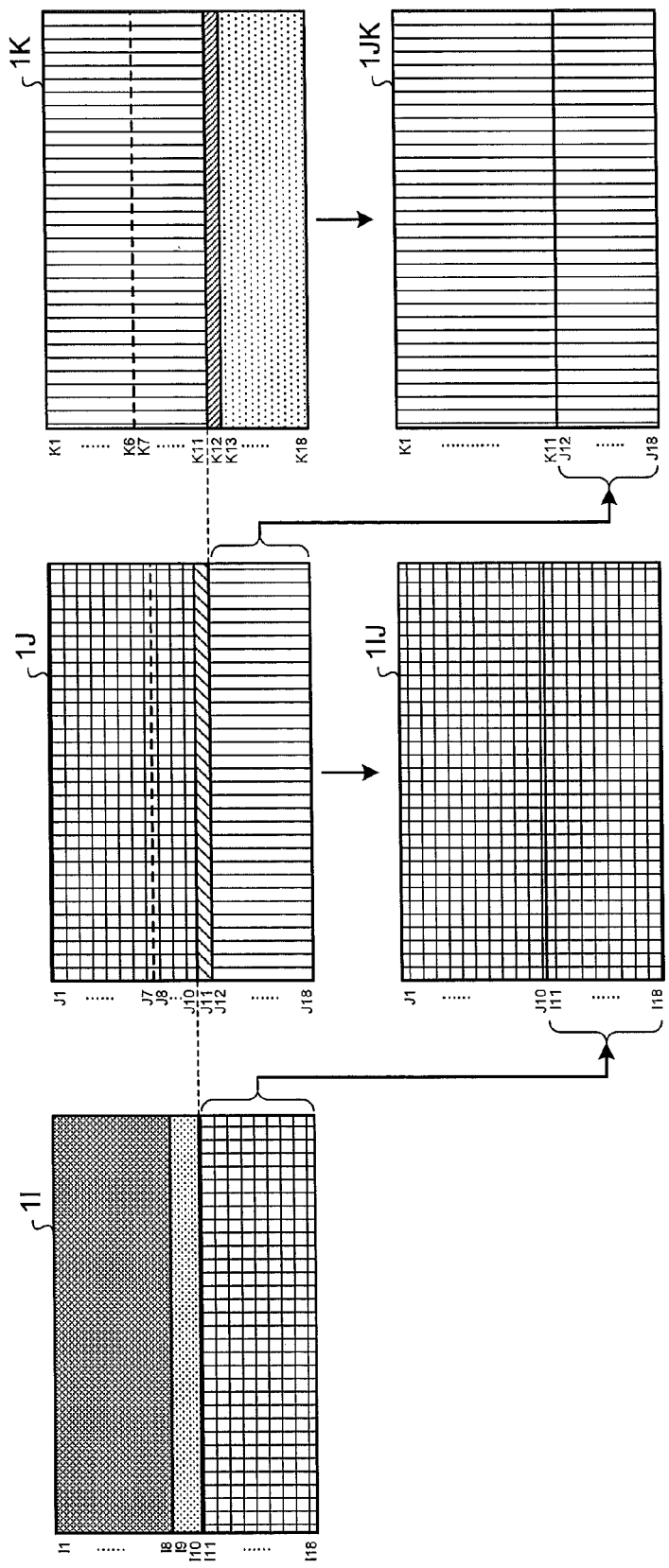
FIG. 4 is a diagram illustrating the overview of a correction process performed in the case illustrated in FIG. 3 by a correction unit included in a control apparatus according to the first embodiment of the present invention.

FIG. 4 is a diagram illustrating the overview of the correction process performed by the correction unit 341 in the case illustrated in FIG. 3. An image 1I will be described first. The exposure amount of an image read by the readout unit 203 in each of readout periods I1 to I8 all equals zero. An image read by the readout unit 203 in a specified readout period is hereinafter referred to as an image in the readout period.

The exposure amount of an image in a readout period Ia (a=9 and 10) corresponds to a (a−8) readout period(s). The readout period Ia is indicated by the same pattern in FIG. 4 for the sake of convenience.

The exposure amount of an image in each of readout periods I11 to I18 corresponds to the pulse illuminated period $T_{1I}$.

The image 1I is the darkest in an area corresponding to the readout periods I1 to I8 and the brightest in an area corresponding to the readout periods I11 to I18.

An image 1J will now be described. The exposure amount of an image in each of readout periods J1 to J7 corresponds to the pulse illuminated period $T_{1I}$.

The exposure amount of an image in each of readout period J8 to J10 equals a sum of the exposure amount corresponding to a part of the pulse illuminated period $T_{1I}$ and the exposure amount corresponding to a part of a pulse illuminated period $T_{1J}$. The sum corresponds to the pulse illuminated period $T_{1J}$.

For example, the exposure amount of the image in the readout period J8 equals a sum of the exposure amount corresponding to two readout periods of the pulse illuminated period $T_{1I}$ and the exposure amount corresponding to one readout period of the pulse illuminated period $T_{1J}$, whereby the sum corresponds to three readout periods.

The exposure amount of an image in a readout period J11 corresponds to four readout periods.

The exposure amount of an image in each of readout periods J12 to J18 corresponds to the pulse illuminated period $T_{1J}$.

The image 1J is the darkest in an area corresponding to the readout periods J1 to J10 and the brightest in an area corresponding to the readout periods J12 to J18.

When correcting the uneven brightness in the image 1J, the correction unit 341 first acquires from the frame memory 342 the image in each of the readout periods I11 to I18 after the pulse illuminated period $T_{1I}$ is over in the frame I. The correction unit 341 then replaces the image in each of the readout periods J11 to J18 in the frame J by the image acquired from the frame memory 342. As a result, a corrected image 1IJ with the uniform exposure amount (corresponding to three readout periods) throughout the screen is generated.

An image 1K will now be described. The exposure amount of an image in each of readout periods K1 to K6 corresponds to the pulse illuminated period $T_{1J}$.

The exposure amount of an image in each of readout periods K7 to K11 equals a sum of the exposure amount corresponding to a part of the pulse illuminated period $T_{1J}$ and the exposure amount corresponding to a part of a pulse illuminated period $T_{1K}$. The sum corresponds to the pulse illuminated period $T_{1J}$.

The exposure amount of an image in a readout period K12 corresponds to six readout periods.

The exposure amount of an image in each of readout periods K13 to K18 corresponds to the pulse illuminated period $T_{1K}$.

The image 1K is the darkest in an area corresponding to the readout periods K1 to K11 and the brightest in an area corresponding to the readout periods K13 to K18.

When correcting the uneven brightness in the image 1K, the correction unit 341 first acquires from the frame memory 342 the image in each of the readout periods J12 to J18 after the pulse illuminated period $T_{1J}$ is over in the frame J. The correction unit 341 then replaces the image in each of the readout periods K12 to K18 in the frame K by the image acquired from the frame memory 342. As a result, a corrected image 1JK with the uniform exposure amount (corresponding to five readout periods) throughout the screen is generated.

Figure 5:
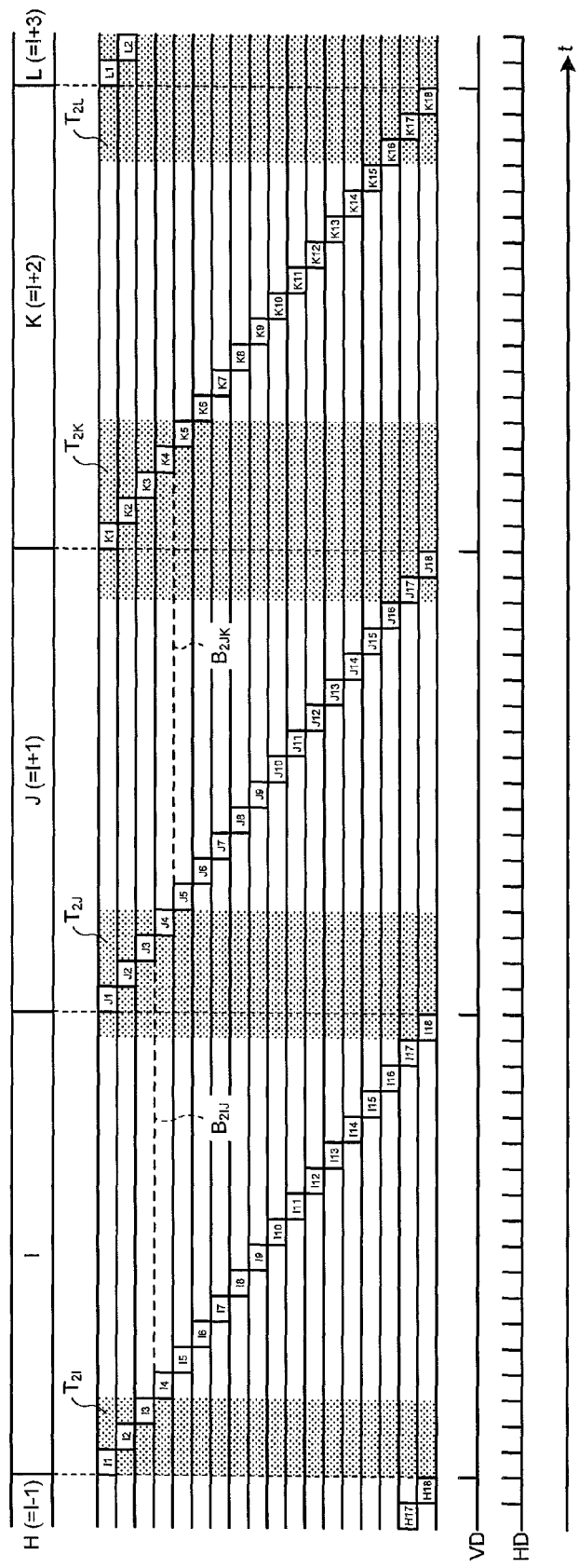
FIG. 5 is a diagram illustrating the overview of an image acquisition method implemented by the endoscope system that is the imaging system according to the first embodiment of the present invention, when the pulse illuminated period gradually increases and straddles two frames.

Now, there will be described a case where the pulse illuminated period straddles two frames. FIG. 5 is a diagram illustrating the overview of an image acquisition method implemented by the endoscope system 1 when the pulse illuminated period gradually increases and straddles two frames.

In the case illustrated in FIG. 5, the exposure amount controller 392 sets an illumination start timing (a first illumination start timing) in the frame I to a starting point of the readout period I1. Accordingly, a second illumination start timing that comes after the first start timing corresponds to a starting point of the readout period I18 in the frame I. Likewise, a third illumination start timing that comes after the second illumination start timing corresponds to a starting point of the readout period J17 in the frame J, while a fourth illumination start timing that comes after the third illumination start timing corresponds to a starting point of the readout period K16 in the frame K.

Note that in the following description, "$T_{2I}$" denotes a pulse illuminated period starting at the first illumination start timing, "$T_{2J}$" denotes a pulse illuminated period starting at the second illumination start timing, "$T_{2K}$" denotes a pulse illuminated period starting at the third illumination start timing, and "$T_{2L}$" denotes a pulse illuminated period starting at the fourth illumination start timing.

A broken line $B_{2IJ}$ illustrated in FIG. 5 indicates an image replacement boundary along which a part of an image read by the readout unit 203 in the frame J is replaced by a corresponding area of an image read by the readout unit 203 in the frame I. Likewise, a broken line $B_{2JK}$ indicates an image replacement boundary along which a part of an image read by the readout unit 203 in the frame K is replaced by a corresponding area of an image read by the readout unit 203 in the frame J.

Figure 6:
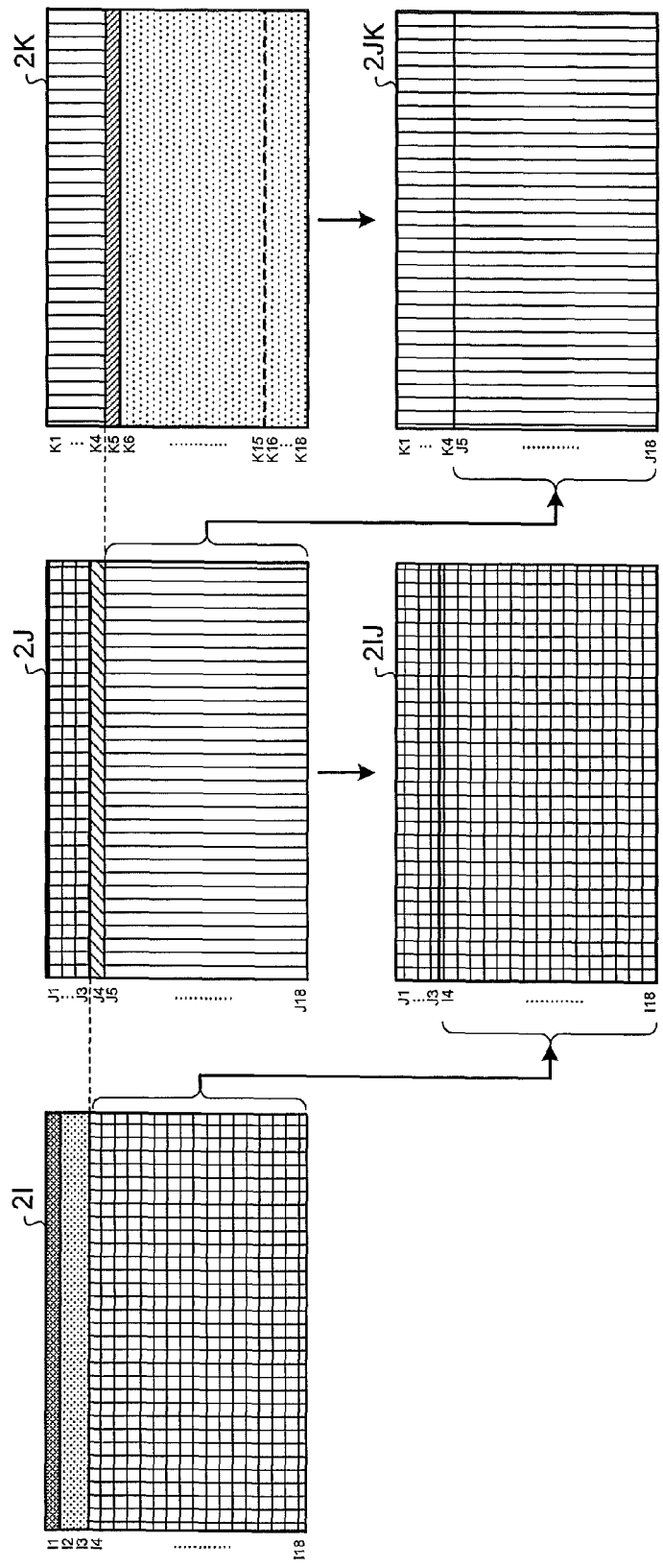
FIG. 6 is a diagram illustrating the overview of a correction process performed in the case illustrated in FIG. 5 by the correction unit included in the control apparatus according to the first embodiment of the present invention.

FIG. 6 is a diagram illustrating the overview of the correction process performed by the correction unit 341 in the case illustrated in FIG. 5. An image 2I will be described first. The exposure amount of an image in the readout period I1 all equals zero. Each of the readout periods I2 and I3 overlaps with a part of the pulse illuminated period $T_{2I}$. The exposure amount of an image read in each of the readout periods I4 to I18 corresponds to the pulse illuminated period $T_{2I}$. The image 2I is the darkest in an area corresponding to the readout period I1 and the brightest in an area corresponding to the readout periods I14 to I18.

An image 2J will now be described. The exposure amount of an image read in each of the readout periods J1 to J3 is equal to a sum of the exposure amount corresponding to a part of the pulse illuminated period $T_{2I}$ and the exposure amount corresponding to a part of the pulse illuminated period $T_{2J}$. The sum corresponds to the pulse illuminated period $T_{2I}$. The exposure amount of an image read in the readout period J4 corresponds to four readout periods. The exposure amount of an image read in each of readout periods J5 to J18 corresponds to the pulse illuminated period $I_{2J}$. The image 2J is the darkest in an area corresponding to the readout periods J1 to J3 and the brightest in an area corresponding to the readout periods J5 to J18.

When correcting the uneven brightness in the image 2J, the correction unit 341 first acquires from the frame memory 342 the image in each of the readout periods I4 to I18 after the pulse illuminated period $T_{2I}$ is over in the frame I. The correction unit 341 then replaces the image in each of the readout periods J4 to J18 in the frame J by the image acquired from the frame memory 342. As a result, a corrected image 2IJ with the uniform exposure amount (corresponding to three readout periods) throughout the screen is generated.

An image 2K will now be described. The exposure amount of an image in each of the readout periods K1 to K4 corresponds to the pulse illuminated period $T_{2J}$. The exposure amount of an image read in the readout period K5 corresponds to six readout periods. The exposure amount of an image read in each of the readout periods K6 to K15 corresponds to the pulse illuminated period $T_{2K}$. The exposure amount of an image in each of the readout periods K16 to K18 is equal to a sum of the exposure amount corresponding to a part of the pulse illuminated period $T_{2J}$ and the exposure amount corresponding to a part of the pulse illuminated period $T_{2K}$. The sum corresponds to the pulse illuminated period $T_{2K}$. The image 2K is the darkest in an area corresponding to the readout periods K1 to K4 and the brightest in an area corresponding to the readout periods K6 to K18.

When correcting the uneven brightness in the image 2K, the correction unit 341 first acquires from the frame memory 342 the image in each of the readout periods J5 to J18 after the pulse illuminated period $T_{2J}$ is over in the frame J. The correction unit 341 then replaces the image in each of the readout periods K5 to K18 in the frame K by the image acquired from the frame memory 342. As a result, a corrected image 2JK with the uniform exposure amount (corresponding to five readout periods) throughout the screen is generated.

(1-2) When the Pulse Illuminated Period Gradually Decreases

Figure 7:
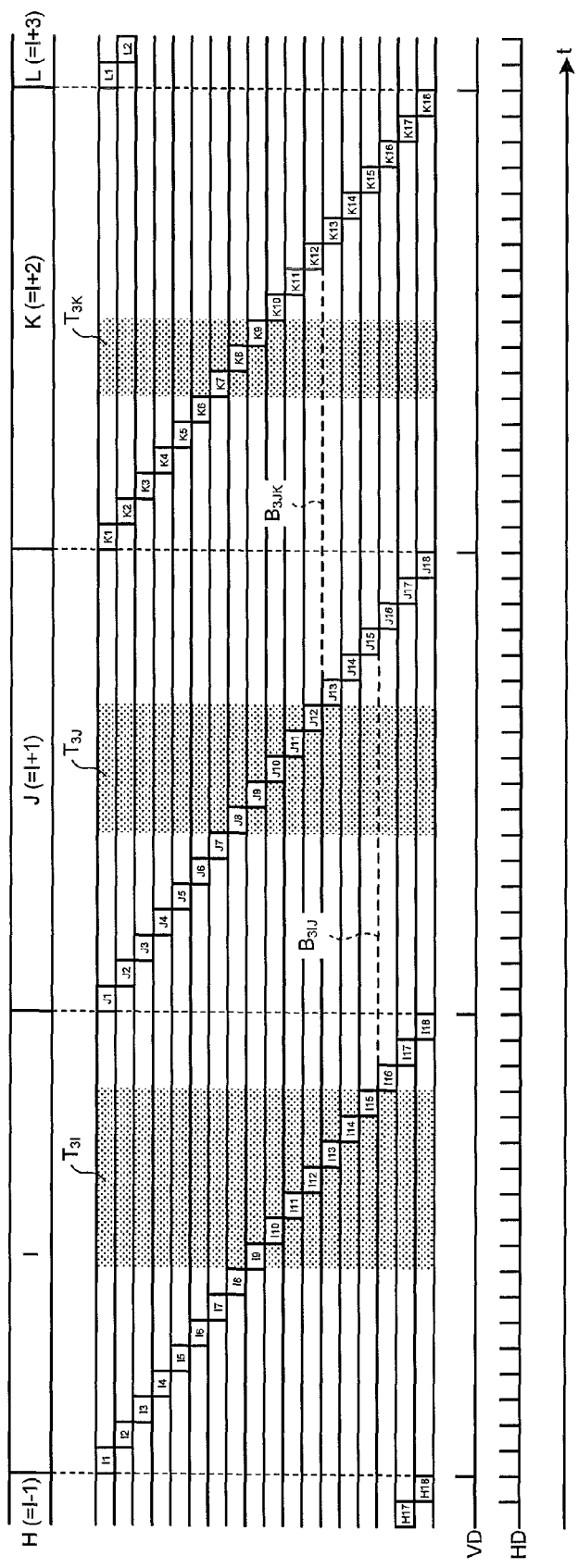
FIG. 7 is a diagram schematically illustrating the overview of an image acquisition method implemented, when the pulse illuminated period gradually decreases, by the endoscope system that is the imaging system according to the first embodiment of the present invention.

FIG. 7 is a diagram schematically illustrating the overview of the image acquisition method implemented by the endoscope system 1 when the pulse illuminated period gradually decreases. In the case illustrated in FIG. 7, the exposure amount controller 392 sets a pulse illumination start timing in the frame I to a starting point of the readout period I9 and sets a pulse illumination start timing in the subsequent frame J to a starting point of the readout period J8. The exposure amount controller 392 further sets a next subsequent pulse illumination start timing to a starting point of the readout period K7 in the frame K.

The duration of a pulse illuminated period $T_{3I}$ in the frame I equals the duration of seven readout periods in the case illustrated in FIG. 7. The duration of a pulse illuminated period $T_{3J}$ in the frame J equals the duration of five readout periods. Moreover, the duration of a pulse illuminated period $T_{3K}$ in the frame K equals the duration of three readout periods. The pulse illuminated period gradually decreases in such manner in FIG. 7.

A broken line $B_{3IJ}$ indicates an image replacement boundary along which a part of an image read by the readout unit 203 in the frame J is replaced by a corresponding area of an image read by the readout unit 203 in the frame I. Likewise, a broken line $B_{3JK}$ indicates an image replacement boundary along which a part of an image read by the readout unit 203 in the frame K is replaced by a corresponding area of an image read by the readout unit 203 in the frame J.

Figure 8:
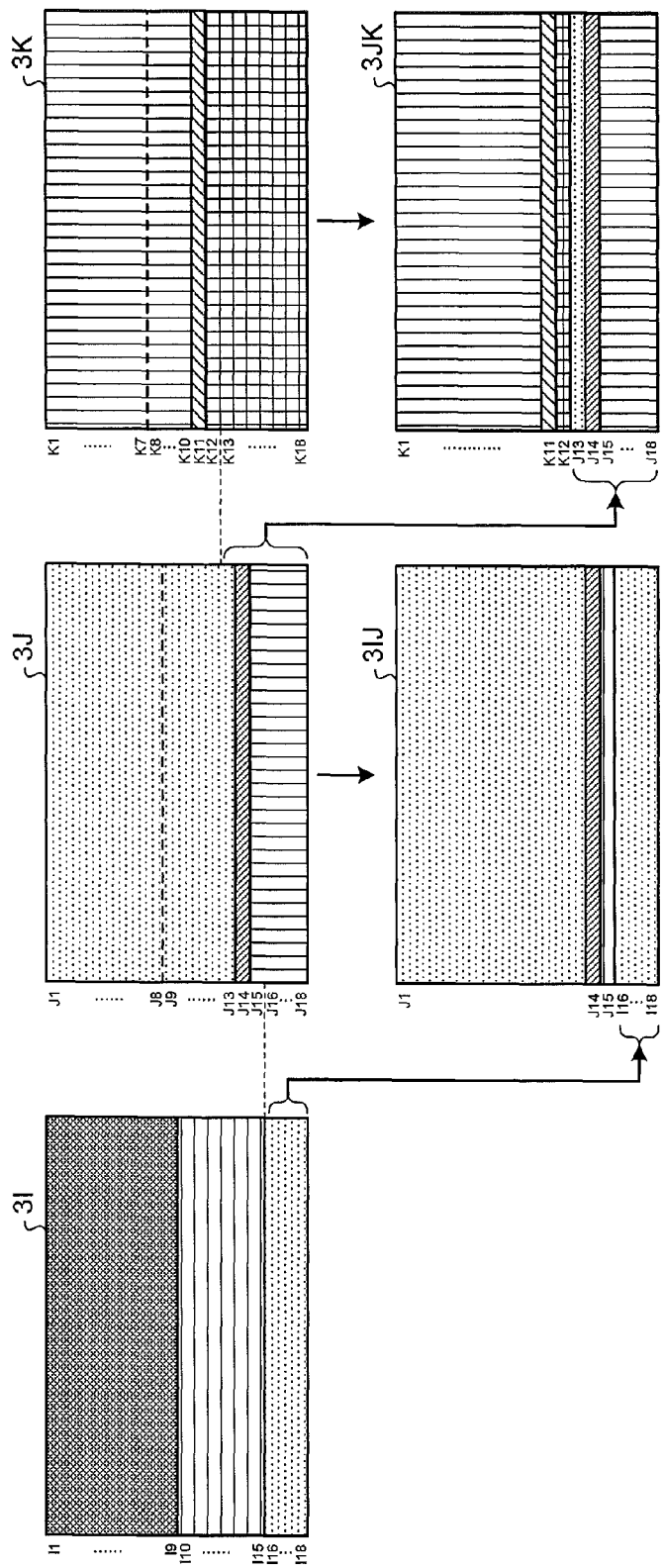
FIG. 8 is a diagram illustrating the overview of a correction process performed in the case illustrated in FIG. 7 by the correction unit included in the control apparatus according to the first embodiment of the present invention.

FIG. 8 is a diagram illustrating the overview of the correction process performed by the correction unit 341 in the case illustrated in FIG. 7. An image 3I will be described first. The exposure amount of an image read in each of the readout periods I1 to I9 all equals zero. The exposure amount of an image read in a readout period Ib (b=10 to 15) corresponds to a (b−9) readout period(s). The readout period Ib is indicated by the same pattern in FIG. 8 for the sake of convenience. The exposure amount of an image read in each of the readout periods I16 to I18 corresponds to the pulse illuminated period $T_{3I}$. The image 3I is the darkest in an area corresponding to the readout periods I1 to I9 and the brightest in an area corresponding to the readout periods I16 to I18.

An image 3J will now be described. The exposure amount of an image read in each of the readout periods J1 to J8 corresponds to the pulse illuminated period $T_{3I}$. The exposure amount of an image read in each of the readout periods J9 to J13 corresponds to a sum of a part of the pulse illuminated period $T_{3I}$ and a part of the pulse illuminated period $T_{3J}$. The sum is equal to the pulse illuminated period $T_{3J}$. The exposure amount of an image read in the readout period J14 corresponds to six readout periods. The exposure amount of an image read in each of the readout periods J15 to J18 corresponds to the pulse illuminated period $T_{3J}$. The image 3J is the brightest in an area corresponding to the readout periods J1 to J13 and the darkest in an area corresponding to the readout periods J15 to J18.

When correcting the uneven brightness in the image 3J, the correction unit 341 first acquires from the frame memory 342 the image in each of the readout periods I16 to I18 after the pulse illuminated period $T_{3I}$ is over in the frame I. The correction unit 341 then replaces the image in each of the readout periods J16 to J18 in the frame J by the image acquired from the frame memory 342. The exposure amount of a corrected image 3IJ acquired by this process is uniform excluding the area of two horizontal lines corresponding to the readout periods J14 and J15.

An image 3K will now be described. The exposure amount of an image in each of the readout periods K1 to K7 corresponds to the pulse illuminated period $T_{3J}$. The exposure amount of an image in each of the readout periods K8 to K10 is equal to a sum of the exposure amount corresponding to a part of the pulse illuminated period $T_{3J}$ and the exposure amount corresponding to a part of the pulse illuminated period $T_{3K}$. The sum corresponds to the pulse illuminated period $T_{3J}$. The exposure amount of an image in the readout period K11 corresponds to four readout periods. The exposure amount of an image in each of the readout periods K12 to K18 corresponds to the pulse illuminated period $T_{3K}$. The image 3K is the brightest in an area corresponding to the readout periods K1 to K10 and the darkest in an area corresponding to the readout periods K12 to K18.

When correcting the uneven brightness in the image 3K, the correction unit 341 first acquires from the frame memory 342 the image in each of the readout periods J13 to J18 after the pulse illuminated period $T_{3J}$ is over in the frame J. The correction unit 341 then replaces the image in each of the readout periods K13 to K18 in the frame K by the image acquired from the frame memory 342. The exposure amount of a corrected image 3JK acquired by this process is uniform excluding the area of four horizontal lines corresponding to the readout periods K11, K12, J13, and J14.

As described above, the uneven brightness cannot always be eliminated completely with use of the corrected image generated by the correction unit 341, when the pulse illuminated period gradually decreases. In such case, there may be provided a limit to the width of decrease of the pulse illuminated period (such as a limit of one readout period or less) in order to bring the exposure amount on the screen closer to the uniform state.

Note that the process performed when the pulse illuminated period gradually decreases and straddles two frames can be performed similarly to what is described in (1-1).

(1-3) When the Pulse Illuminated Period is Fixed

Figure 9:
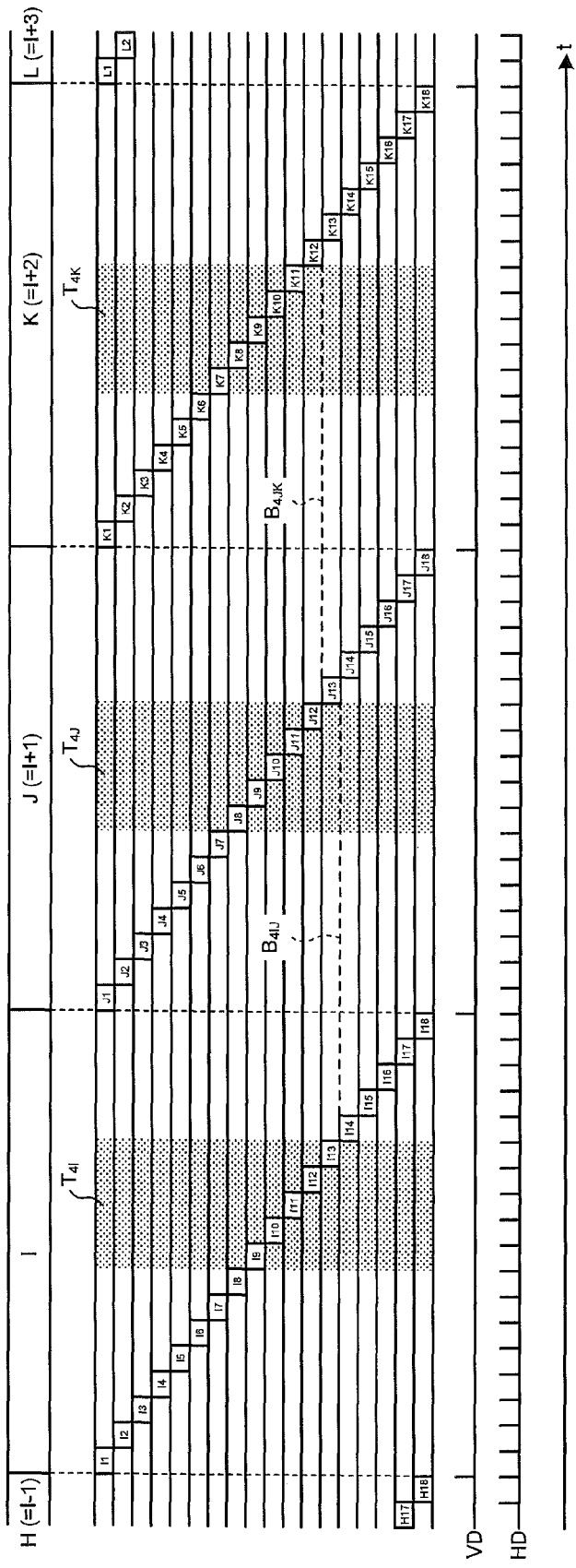
FIG. 9 is a diagram schematically illustrating the overview of an image acquisition method implemented, when the pulse illuminated period is fixed, by the endoscope system that is the imaging system according to the first embodiment of the present invention.

FIG. 9 is a diagram schematically illustrating the overview of the image acquisition method implemented by the endoscope system 1 when the pulse illuminated period is fixed. Note that the exposure amount controller 392 sets the illumination start timing in the manner similar to that described in (1-1).

In the case illustrated in FIG. 9, the duration of each of a pulse illuminated period $T_{4I}$ in the frame I, a pulse illuminated period $T_{4J}$ in the frame J, and a pulse illuminated period $T_{4K}$ in the frame K is equal to the duration of five readout periods. A broken line $B_{4IJ}$ indicates an image replacement boundary along which a part of an image read by the readout unit 203 in the frame J is replaced by a corresponding area of an image read by the readout unit 203 in the frame I. Likewise, a broken line $B_{4JK}$ indicates an image replacement boundary along which a part of an image read by the readout unit 203 in the frame K is replaced by a corresponding area of an image read by the readout unit 203 in the frame J.

Figure 10:
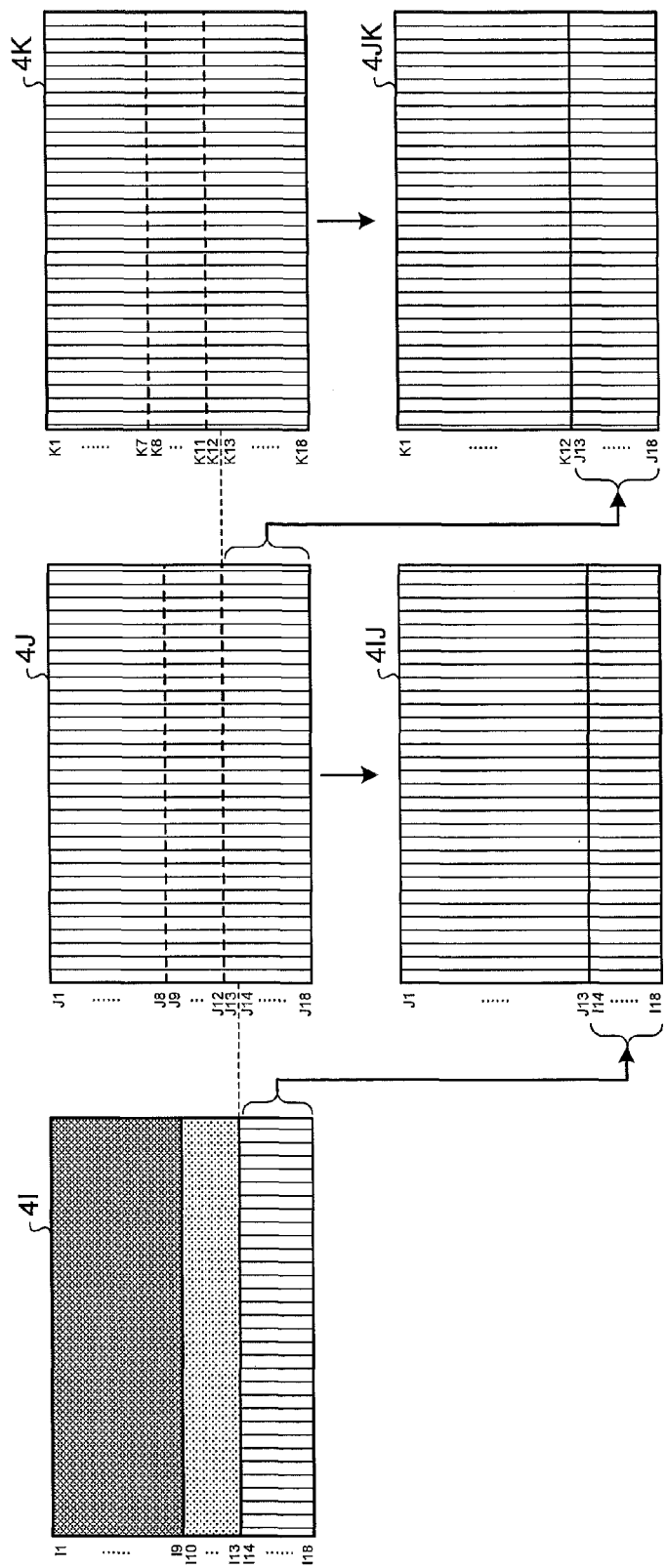
FIG. 10 is a diagram illustrating the overview of a correction process performed in the case illustrated in FIG. 9 by the correction unit included in the control apparatus according to the first embodiment of the present invention.

FIG. 10 is a diagram illustrating the overview of the correction process performed by the correction unit 341 in the case illustrated in FIG. 9. An image 4I will be described first. The exposure amount of an image in each of the readout periods I1 to I9 all equals zero. The exposure amount of an image in a readout period Ic (c=10 to 13) corresponds to a (c−9) readout period(s). The readout period Ic is indicated by the same pattern in FIG. 10 for the sake of convenience. The exposure amount of an image in each of the readout periods I14 to I18 corresponds to the pulse illuminated period $T_{4I}$. The image 4I is the darkest in an area corresponding to the readout periods I1 to I9 and the brightest in an area corresponding to the readout periods I14 to I18.

An image 4J will now be described. The exposure amount of an image in each of the readout periods J1 to J8 corresponds to the pulse illuminated period $T_{4I}$. The exposure amount of an image in each of the readout periods J9 to J12 is equal to a sum of the exposure amount corresponding to a part of the pulse illuminated period $T_{4I}$ and the exposure amount corresponding to a part of the pulse illuminated period T. The sum corresponds to the pulse illuminated period $T_{4I}$. The exposure amount of an image in each of the readout periods J13 to J18 corresponds to the pulse illuminated period $T_{4J}$. The exposure amount of the image 4J is uniform (corresponding to five readout periods) throughout the screen.

The correction unit 341 first acquires from the frame memory 342 the image in each of the readout periods I14 to I18 after the pulse illuminated period $T_{4I}$ is over in the frame I. The correction unit 341 then replaces the image in each of the readout periods J14 to J18 in the frame J by the image acquired from the frame memory 342. A corrected image 4IJ with the uniform exposure amount (corresponding to five readout periods) throughout the screen is generated as a result of this process.

An image 4K will now be described. The exposure amount of an image in each of the readout periods K1 to K7 corresponds to the pulse illuminated period $T_{4J}$. The exposure amount of an image in each of the readout periods K8 to K11 is equal to a sum of the exposure amount corresponding to a part of the pulse illuminated period $T_{4J}$ and the exposure amount corresponding to a part of the pulse illuminated period $T_{4K}$. The sum corresponds to the pulse illuminated period $T_{4J}$. The exposure amount of an image in each of the readout periods K12 to K18 corresponds to the pulse illuminated period $T_{4K}$. The exposure amount of the image 4K is uniform (corresponding to five readout periods) throughout the screen.

The correction unit 341 first acquires from the frame memory 342 the image in each of the readout periods J13 to J18 after the pulse illuminated period $T_{4J}$ is over in the frame J. The correction unit 341 then replaces the image in each of the readout periods K13 to K18 in the frame K by the image acquired from the frame memory 342. As a result, a corrected image 4JK with the uniform exposure amount (corresponding to five readout periods) throughout the screen is generated.

The exposure amount of each of the images 4J and 4K is uniform throughout the screen. The first embodiment may thus be adapted to not perform the correction process by the correction unit 341 when the pulse illuminated period is fixed.

The first embodiment of the present invention as described above performs the control to have the different timings at which the illumination light is radiated between the first picture period in which the image pickup device performs the reading and the second picture period succeeding the first picture period, whereby the image having appropriate brightness and reduced uneven brightness can be generated even when there is no period in which the image pickup device simultaneously performs exposure on all the horizontal lines in capturing an image of the subject while illuminating the pulsed illumination light in each of the successive picture periods.

Moreover, in the first embodiment, the exposure amount controller 392 sets the cycle of the timing, at which the pulse illuminated period by the light source device 4 is started, to be shorter than the cycle of the single frame by one readout period, while the correction unit 341 replaces the image in the latest frame (the second picture period) by the corresponding image being read after the pulse illuminated period in the preceding frame (the first picture period) is over. Accordingly, the reduced exposure amount in the area due to the overlap between the readout period of the image pickup device and the pulse illumination timing can be complemented by the pulse illumination in the following frame. As a result, the image with less uneven brightness can be generated by having the substantially uniform exposure time in all the horizontal lines.

The uneven brightness cannot be complemented completely in the first embodiment when there is excessive change in the brightness as in the case where the pulse illuminated period gradually decreases (refer to (1-2)). This however is not a big problem in the practical use because the uneven brightness can be eliminated completely in the subsequent steady state where the brightness is fixed (refer to (1-3)).

Second Embodiment

Next, the second embodiment of the present invention will be described. The configuration of an endoscope system that is an imaging system according to the second embodiment of the present invention is similar to the configuration of the endoscope system 1 described above. Now, there will be described the overview of a process performed when a moving image is shot by an endoscope system 1 according to the second embodiment.

Similar to the first embodiment, an exposure amount controller 392 sets a cycle of a timing, at which the pulse illumination by a light source device 4 ends, to be shorter than a cycle of a single frame by the duration equal to one readout period. Under control of a correction controller 391, a correction unit 341 generates a corrected image by replacing an area of an imaging signal being read in the latest frame (a second picture period) by a readout unit 203 with a recorded image, the area corresponding to the recorded image that is read after a pulse illuminated period is started in a preceding frame (a first picture period) and recorded in a frame memory 342.

The overview of a correction process performed by the correction unit 341 will be described below by cases where: (2-1) the pulse illuminated period gradually decreases; (2-2) the pulse illuminated period gradually increases; and (2-3) the pulse illuminated period is fixed.

(2-1) When the Pulse Illuminated Period Gradually Decreases

Figure 11:
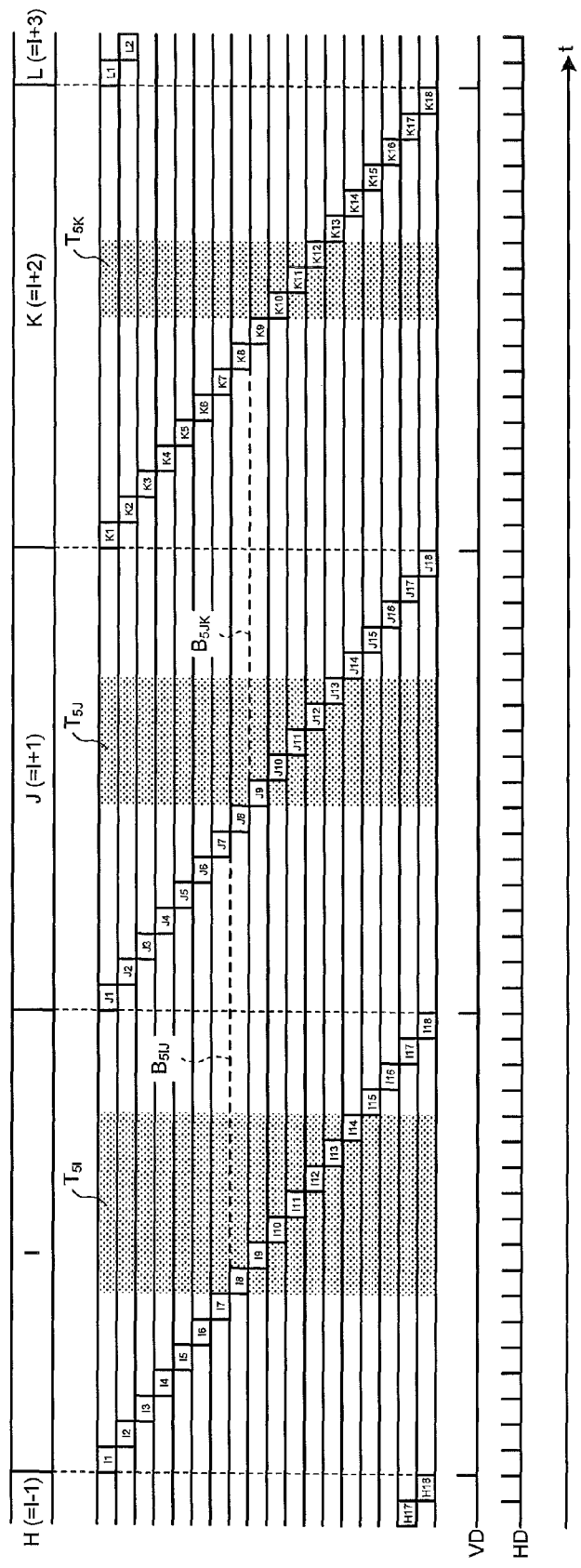
FIG. 11 is a diagram schematically illustrating the overview of an image acquisition method implemented, when a pulse illuminated period gradually decreases, by an endoscope system that is an imaging system according to a second embodiment of the present invention.

FIG. 11 is a diagram schematically illustrating the overview of an image acquisition method implemented by the endoscope system 1 when the pulse illuminated period gradually decreases. In the case illustrated in FIG. 11, the exposure amount controller 392 sets a pulse illumination end timing in a frame I to an end point of a readout period I14, and sets a pulse illumination end timing in a frame J to an end point of a readout period J13 in the frame J. Moreover, the exposure amount controller 392 sets a pulse illumination end timing in a frame K succeeding the frame J to an end point of a readout period K12 in the frame K.

The duration of a pulse illuminated period $T_{5I}$ in the frame I in FIG. 11 equals the duration of seven readout periods. The duration of a pulse illuminated period $T_{5J}$ in the frame J equals the duration of five readout periods. Moreover, the duration of a pulse illuminated period $T_{5K}$ in the frame K equals the duration of three readout periods. It is needless to say that such setting of the pulse illuminated period is merely provided as an example.

A broken line $B_{5IJ}$ indicates an image replacement boundary along which a part of an image read by the readout unit 203 in the frame J is replaced by a corresponding area of an image read by the readout unit 203 in the frame I. Likewise, a broken line $B_{5JK}$ indicates an image replacement boundary along which a part of an image read by the readout unit 203 in the frame K is replaced by a corresponding area of an image read by the readout unit 203 in the frame J.

Figure 12:
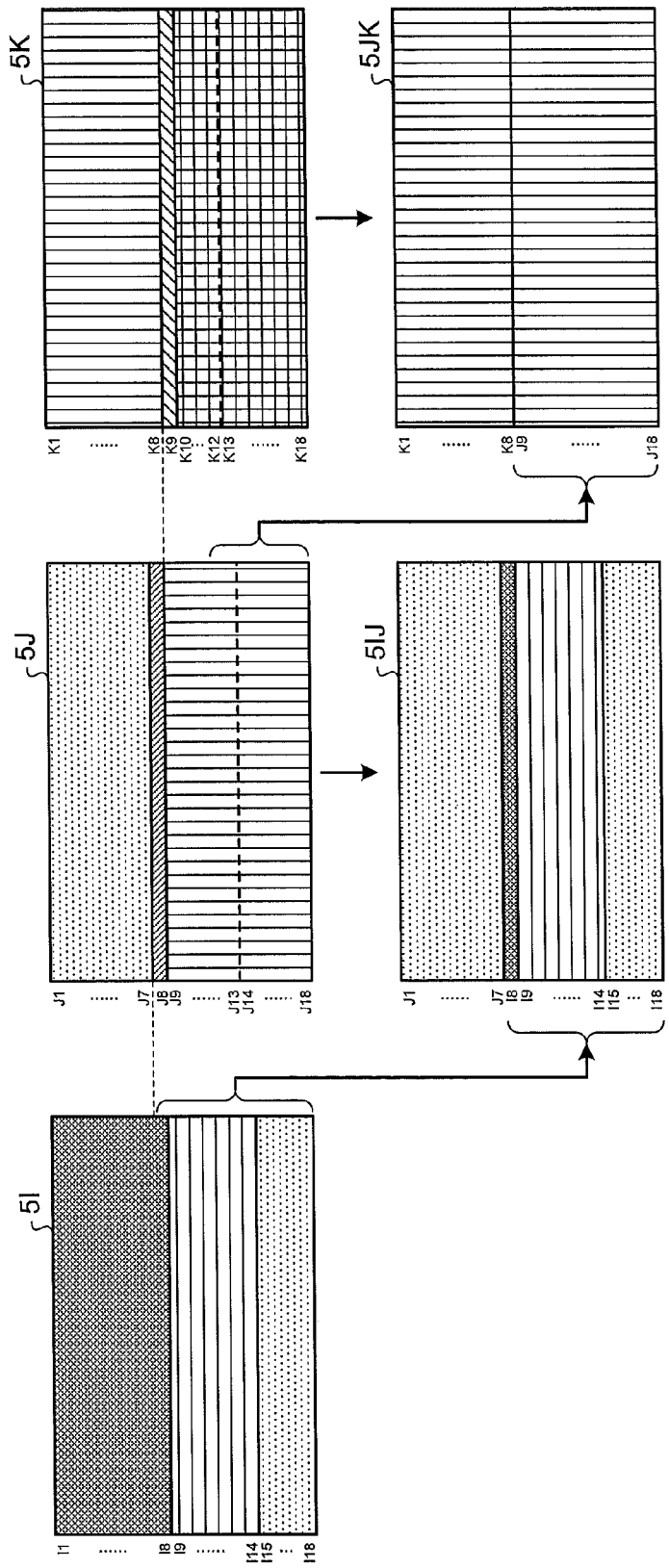
FIG. 12 is a diagram illustrating the overview of a correction process performed in the case illustrated in FIG. 11 by a correction unit included in a control apparatus according to the second embodiment of the present invention.

FIG. 12 is a diagram illustrating the overview of the correction process performed by the correction unit 341 in the case illustrated in FIG. 11. An image 5I will be described first. The exposure amount of an image in each of readout periods I1 to I8 all equals zero. The exposure amount of an image in a readout period Id (d=9 to 14) corresponds to a (d−8) readout period(s). The readout period Id is indicated by the same pattern in FIG. 12 for the sake of convenience. The exposure amount of an image in each of readout periods I15 to I18 corresponds to the pulse illuminated period $T_{5I}$. The image 5I is the darkest in an area corresponding to the readout periods I1 to I8 and the brightest in an area corresponding to the readout periods I15 to I18.

An image 5J will now be described. The exposure amount of an image in each of readout periods J1 to J7 corresponds to the pulse illuminated period $T_{5I}$. The exposure amount of an image in a readout period J8 corresponds to six readout periods. The exposure amount of an image in a readout period J9 corresponds to five readout periods. The exposure amount of an image in each of readout periods J10 to J13 is equal to a sum of the exposure amount corresponding to a part of the pulse illuminated period $T_{5I}$ and the exposure amount corresponding to a part of the pulse illuminated period $T_{5J}$. The sum corresponds to the pulse illuminated period $T_{5J}$. The exposure amount of an image in each of readout periods J14 to J18 corresponds to the pulse illuminated period $T_{5J}$. The image 5J is the brightest in an area corresponding to the readout periods J1 to J7 and the darkest in an area corresponding to the readout periods J9 to J18.

The correction unit 341 first acquires from the frame memory 342 the image in each of the readout periods I8 to I18 after the pulse illuminated period $T_{5I}$ is started in the frame I. The correction unit 341 then replaces the image in each of the readout periods J8 to J18 in the frame J by the image acquired from the frame memory 342. The exposure amount of a corrected image 5IJ acquired from the first correction process performed after the pulse is illuminated is uniform only in the area corresponding to the readout periods J1 to J7 and I15 to I18.

An image 5K will now be described. The exposure amount of an image in each of readout periods K1 to K8 corresponds to the pulse illuminated period $T_{5J}$. The exposure amount of an image in a readout period K9 corresponds to four readout periods. The exposure amount of an image in a readout period K10 corresponds to three readout periods. The exposure amount of an image in each of readout periods K11 and K12 is equal to a sum of the exposure amount corresponding to a part of the pulse illuminated period $T_{5J}$ and the exposure amount corresponding to a part of the pulse illuminated period $T_{5K}$. The sum corresponds to the pulse illuminated period $T_{5K}$. The exposure amount of an image in each of readout periods K13 to K18 corresponds to the pulse illuminated period $T_{5K}$. The image 5K is the brightest in an area corresponding to the readout periods K1 to K8 and the darkest in an area corresponding to the readout periods K10 to K18.

When correcting the uneven brightness in the image 5K, the correction unit 341 first acquires from the frame memory 342 the image in each of the readout periods J9 to J18 after the pulse illuminated period $T_{5J}$ is started in the frame J. The correction unit 341 then replaces the image in each of the readout periods K9 to K18 in the frame K by the imaging signal acquired from the frame memory 342. As a result, a corrected image 5JK with the uniform exposure amount (corresponding to five readout periods) throughout the screen is generated.

(2-2) When the Pulse Illuminated Period Gradually Increases

Figure 13:
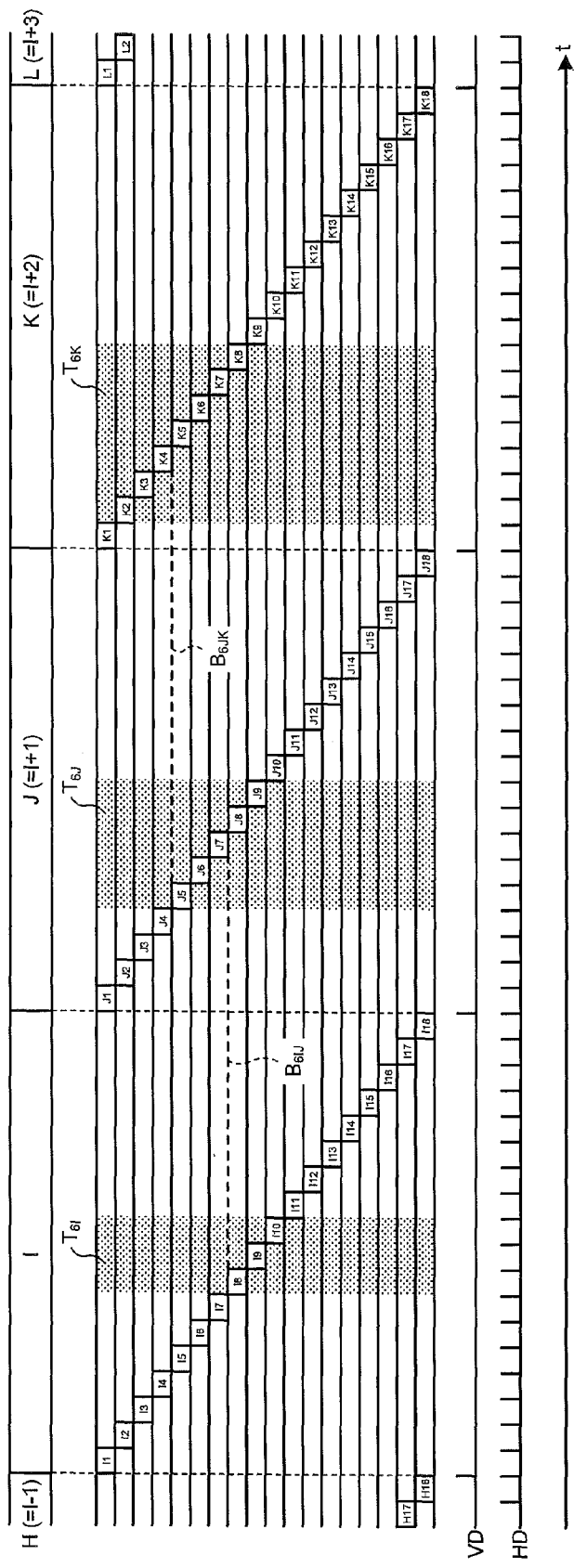
FIG. 13 is a diagram schematically illustrating the overview of an image acquisition method implemented, when the pulse illuminated period gradually increases, by the endoscope system that is the imaging system according to the second embodiment of the present invention.

FIG. 13 is a diagram schematically illustrating the overview of an image acquisition method implemented by the endoscope system 1 when the pulse illuminated period gradually increases. In the case illustrated in FIG. 13, the exposure amount controller 392 sets a pulse illumination end timing in the frame I to an end point of the readout period I10, and sets a subsequent pulse illumination end timing to an end point of the readout period J9 in the frame J. The exposure amount controller 392 further sets a next subsequent pulse illumination end timing to an end point of the readout period K8 in the frame K.

In the case illustrated in FIG. 13, the duration of a pulse illuminated period $I_{6I}$ in the frame I equals the duration of three readout periods. The duration of a pulse illuminated period $T_{6J}$ in the frame J equals the duration of five readout periods. Moreover, the duration of a pulse illuminated period $T_{6K}$ in the frame K equals the duration of seven readout periods.

A broken line $B_{6IJ}$ indicates an image replacement boundary along which a part of an image read by the readout unit 203 in the frame J is replaced by a corresponding area of an image read by the readout unit 203 in the frame I. Likewise, a broken line $B_{6JK}$ indicates an image replacement boundary along which a part of an image read by the readout unit 203 in the frame K is replaced by a corresponding area of an image read by the readout unit 203 in the frame J.

Figure 14:
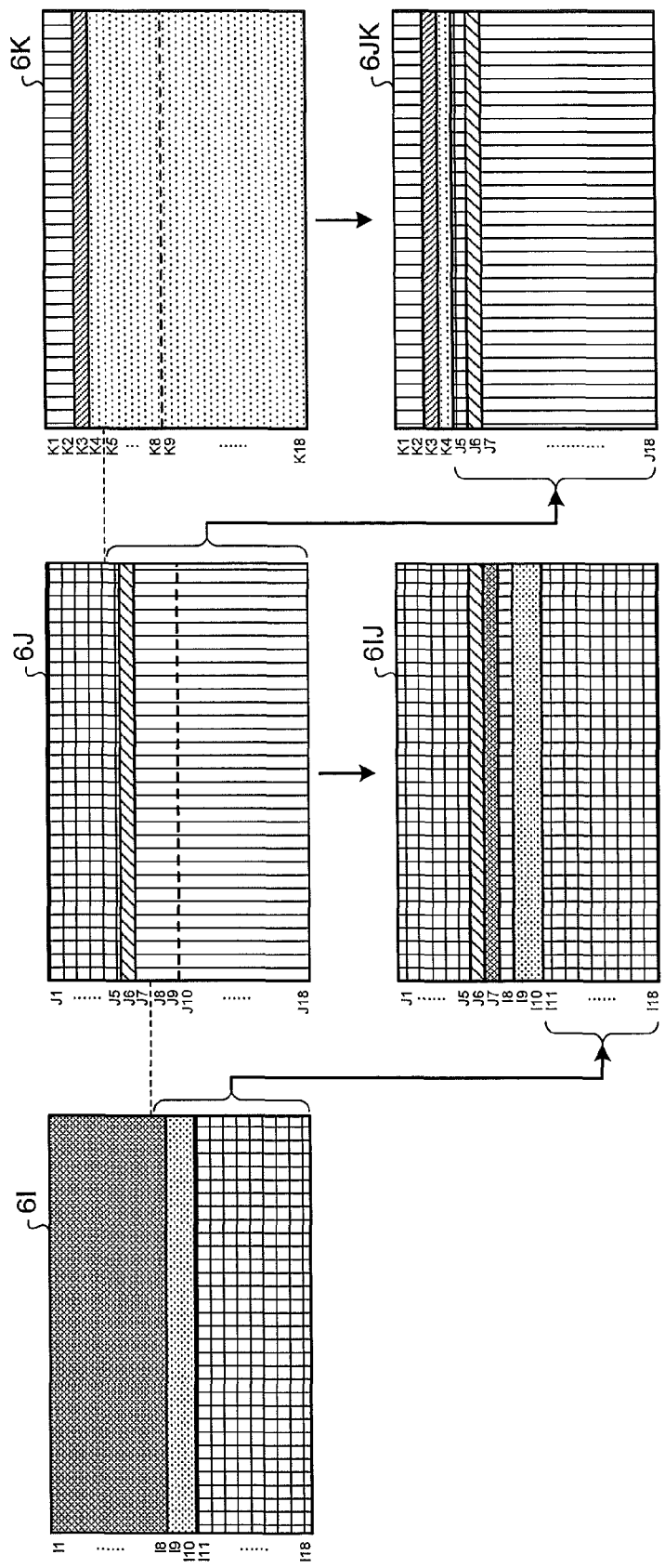
FIG. 14 is a diagram illustrating the overview of a correction process performed in the case illustrated in FIG. 13 by the correction unit included in the control apparatus according to the second embodiment of the present invention.

FIG. 14 is a diagram illustrating the overview of the correction process performed by the correction unit 341 in the case illustrated in FIG. 13. An image 6I will be described first. The exposure amount of an image in each of the readout periods I1 to I8 all equals zero. The exposure amount of an image in a readout period Ie (e=9 and 10) corresponds to a (e−8) readout period(s). The readout period Ie is indicated by the same pattern in FIG. 14 for the sake of convenience. The exposure amount of an image in each of the readout periods I11 to I18 corresponds to the pulse illuminated period $T_{6I}$. The image 6I is the darkest in an area corresponding to the readout periods I1 to I8 and the brightest in an area corresponding to the readout periods I11 to I18.

An image 6J will now be described. The exposure amount of an image in each of the readout periods J1 to J5 corresponds to the pulse illuminated period $T_{6I}$. The exposure amount of an image in the readout period J6 corresponds to four readout periods. The exposure amount in each of the readout periods J7 to J9 equals a sum of the exposure amount corresponding to a part of the pulse illuminated period $T_{6I}$ and the exposure amount corresponding to a part of the pulse illuminated period $T_{6J}$. The sum corresponds to the pulse illuminated period $T_{6J}$. The exposure amount of an image in each of the readout periods J10 to J18 corresponds to the pulse illuminated period $T_{6J}$. The image 6J is the darkest in an area corresponding to the readout periods J1 to J5 and the brightest in an area corresponding to the readout periods J7 to J18.

The correction unit 341 first acquires from the frame memory 342 the image in each of the readout periods I8 to I18 after the pulse illuminated period $T_{6I}$ is started in the frame I. The correction unit 341 then generates a corrected image 6I and K2 corresponds to the pulse illuminated period $T_{6J}$. The exposure amount of an image in the readout period K3 corresponds to six readout periods. The exposure amount of an image in each of the readout periods K4 to K8 equals a sum of the exposure amount corresponding to a part of the pulse illuminated period $T_{6J}$ and the exposure amount corresponding to a part of the pulse illuminated period $T_{6K}$. The sum corresponds to the pulse illuminated period $T_{6K}$. The exposure amount of an image in each of the readout periods K9 to K18 corresponds to the pulse illuminated period $T_{6K}$. The image 6K is the darkest in an area corresponding to the readout periods K1 and K2 and the brightest in an area corresponding to the readout periods K4 to K18.

The correction unit 341 first acquires from the frame memory 342 the image in each of the readout periods J5 to J18 after the pulse illuminated period $T_{6J}$ is started in the frame J. The correction unit 341 then generates a corrected image 6JK by replacing the image in each of the readout periods K5 to K18 in the frame K by the image acquired from the frame memory 342. The exposure amount of the corrected image 6JK is uniform excluding the area corresponding to the readout periods K3, K4, and J5 to J7.

As described above, the corrected image generated by the correction unit 341 cannot completely eliminate the uneven brightness in some cases when in the excessive state where the pulse illuminated period gradually increases. In such case, there may be provided a limit to the width of increase of the pulse illuminated period (such as a limit of one readout period or less) in order to bring the exposure amount on the screen closer to the uniform state.

(2-3) When the Pulse Illuminated Period is Fixed

Figure 15:
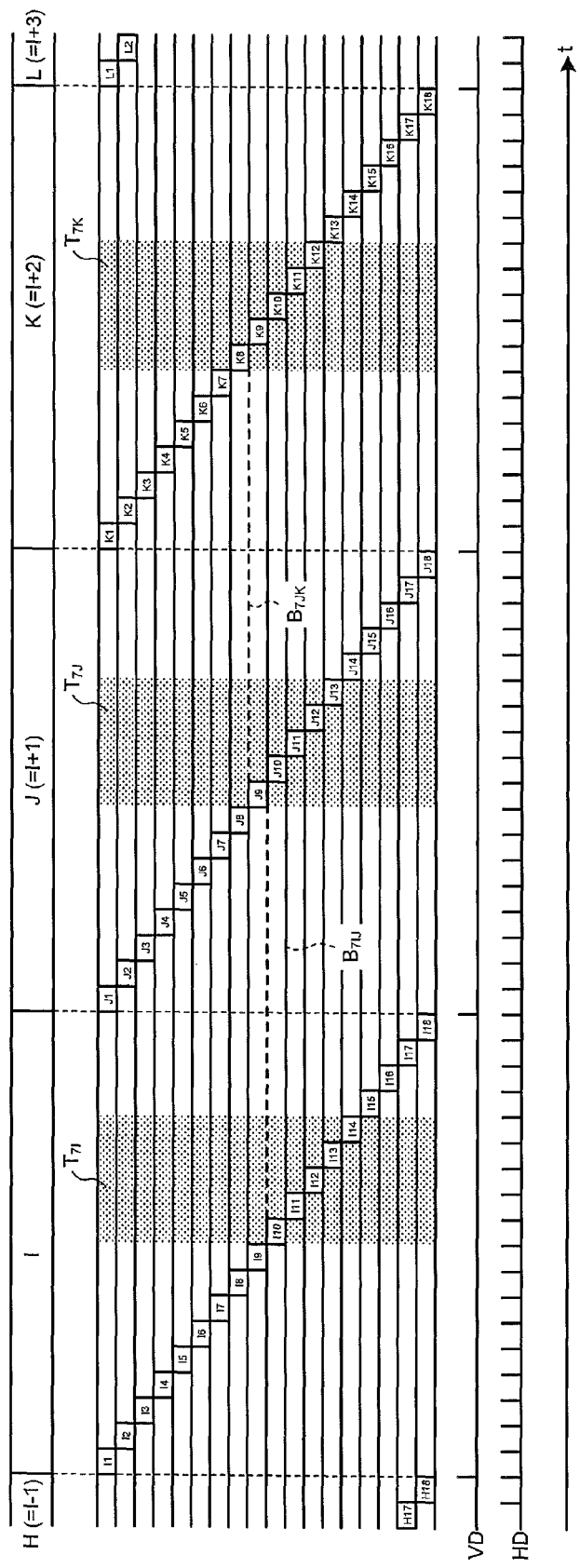
FIG. 15 is a diagram schematically illustrating the overview of an image acquisition method implemented, when the pulse illuminated period is fixed, by the endoscope system that is the imaging system according to the second embodiment of the present invention.

FIG. 15 is a diagram schematically illustrating the overview of the image acquisition method implemented by the endoscope system 1 when the pulse illuminated period is fixed. Note that the exposure amount controller 392 sets the illumination end timing in the same way as that described in (2-1).

In the case illustrated in FIG. 15, the duration of each of a pulse illuminated period $T_{7I}$ in the frame I, a pulse illuminated period $T_{7J}$ in the frame J, and a pulse illuminated period $T_{7K}$ in the frame K all equals the duration of five readout periods. A broken line $B_{7IJ}$ indicates an image replacement boundary along which a part of an image read by the readout unit 203 in the frame J is replaced by a corresponding area of an image read by the readout unit 203 in the frame I. Likewise, a broken line $B_{7JK}$ indicates an image replacement boundary along which a part of an image read by the readout unit 203 in the frame K is replaced by a corresponding area of an image read by the readout unit 203 in the frame J.

Figure 16:
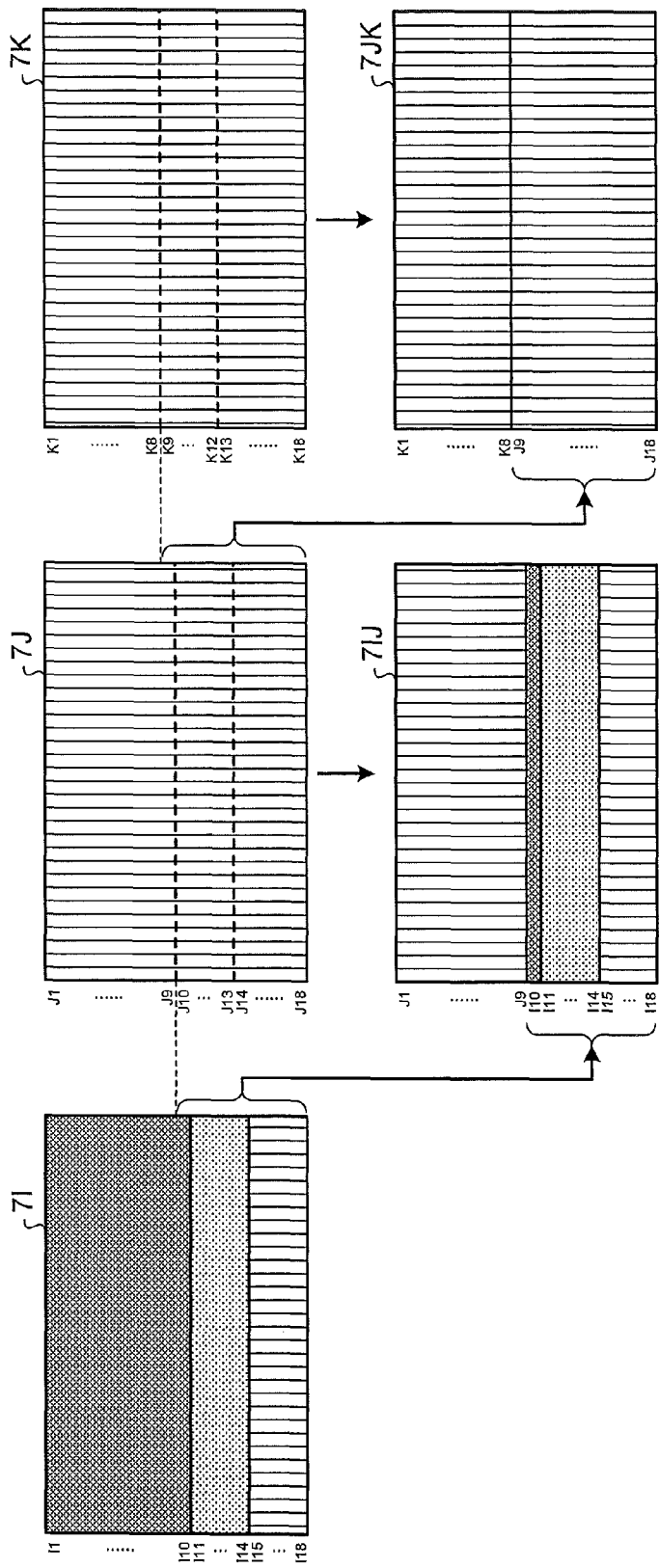
FIG. 16 is a diagram illustrating the overview of a correction process performed in the case illustrated in FIG. 15 by the correction unit included in the control apparatus according to the second embodiment of the present invention.

FIG. 16 is a diagram illustrating the overview of the correction process performed by the correction unit 341 in the case illustrated in FIG. 15. An image 7I will be described first. The exposure amount of an image in each of the readout periods I1 to I10 all equals zero. The exposure amount of an image in a readout period If (d=11 to I4) corresponds to a (f−9) readout period(s). The readout period If is indicated by the same pattern in FIG. 16 for the sake of convenience. The exposure amount of an image in each of the readout periods I15 to I18 corresponds to the pulse illuminated period $T_{7I}$. The image 7I is the darkest in an area corresponding to the readout periods I1 to I10 and the brightest in an area corresponding to the readout periods I15 to I18.

An image 7J will now be described. The exposure amount of an image in each of the readout periods J1 to J9 corresponds to the pulse illuminated period $T_{7J}$. The exposure amount of an image in each of the readout periods J10 to J13 is equal to a sum of the exposure amount corresponding to a part of the pulse illuminated period $T_{7I}$ and the exposure amount corresponding to a part of the pulse illuminated period $T_{7J}$. The sum corresponds to the pulse illuminated period $T_{7I}$. The exposure amount of an image in each of the readout periods J14 to J18 corresponds to the pulse illuminated period $T_{7J}$. The exposure amount of the image 7J is uniform (corresponding to five readout periods) throughout the screen.

The correction unit 341 first acquires from the frame memory 342 the image in each of the readout periods I10 to I18 after the pulse illuminated period $T_{7I}$ is started in the frame I. The correction unit 341 then generates a corrected image 7IJ by replacing the image in each of the readout periods J10 to J18 in the frame J by the image acquired from the frame memory 342. The exposure amount of the corrected image 7IJ is uniform excluding the area corresponding to the readout periods I10 to I14.

An image 7K will now be described. The exposure amount of an image in each of the readout periods K1 to K8 corresponds to the pulse illuminated period $T_{7J}$. The exposure amount of an image in each of the readout periods K9 to K12 is equal to a sum of the exposure amount corresponding to a part of the pulse illuminated period $T_{7J}$ and the exposure amount corresponding to a part of the pulse illuminated period $T_{7K}$. The sum corresponds to the pulse illuminated period $T_{7J}$. The exposure amount of an image in each of the readout periods K13 to K18 corresponds to the pulse illuminated period $T_{7K}$. The exposure amount of the image 7K is uniform (corresponding to five readout periods) throughout the screen.

The correction unit 341 acquires from the frame memory 342 the image in each of the readout periods J9 to J18 after the pulse illuminated period $T_{7J}$ is over in the frame J. The correction unit 341 then replaces the image in each of the readout periods K9 to K18 in the frame K by the imaging signal acquired from the frame memory 342. As a result, a corrected image 7JK with the uniform exposure amount (corresponding to five readout periods) throughout the screen is generated.

Note that the exposure amount of each of the images 7J and 7K is uniform throughout the screen. The second embodiment may therefore be adapted such that the correction unit 341 does not perform the correction process when the pulse illuminated period is fixed.

Similar to the first embodiment, the second embodiment of the present invention as described above can generate the image having appropriate brightness and reduced uneven brightness even when there is no period in which the image pickup device simultaneously performs exposure on all the horizontal lines in capturing an image of the subject while illuminating the pulsed illumination light in each of the successive picture periods.

Moreover, in the second embodiment, the exposure amount controller 392 sets the cycle of the timing, at which the pulse illuminated period by the light source device 4 is started, to be shorter than the cycle of the single frame by one readout period, while the correction unit 341 replaces the image in the latest frame (the second picture period) by the corresponding image being read after the starting point of the pulse illuminated period in the preceding frame (the first picture period). Accordingly, the reduced exposure amount in the area due to the overlap between the readout period of the image pickup device and the pulse illumination timing can be complemented by the pulse illumination in the following frame. As a result, the image with less uneven brightness can be generated by having the substantially uniform exposure time in all the horizontal lines.

The uneven brightness cannot be complemented completely in the second embodiment when there is excessive change in the brightness as in the case where the pulse illuminated period gradually increases (refer to (2-2)). This however is not a big problem in the practical use because the uneven brightness can be eliminated completely in the subsequent steady state where the brightness is fixed (refer to (2-3)).

Third Embodiment

Next, the third embodiment of the present invention will be described. The configuration of an endoscope system that is an imaging system according to the third embodiment of the present invention is similar to the configuration of the endoscope system 1 described above. Now, there will be described the overview of a process performed when a moving image is shot by an endoscope system 1 according to the third embodiment.

A blanking period is provided at the end of a frame in the third embodiment. In this case, the exposure amount increases by the amount corresponding to the blanking period when the pulse illuminated period includes the blanking period. Accordingly, the third embodiment performs a process of making the brightness level even with another area by a correction unit 341 correcting the exposure amount increased by the blanking period.

Figure 17:
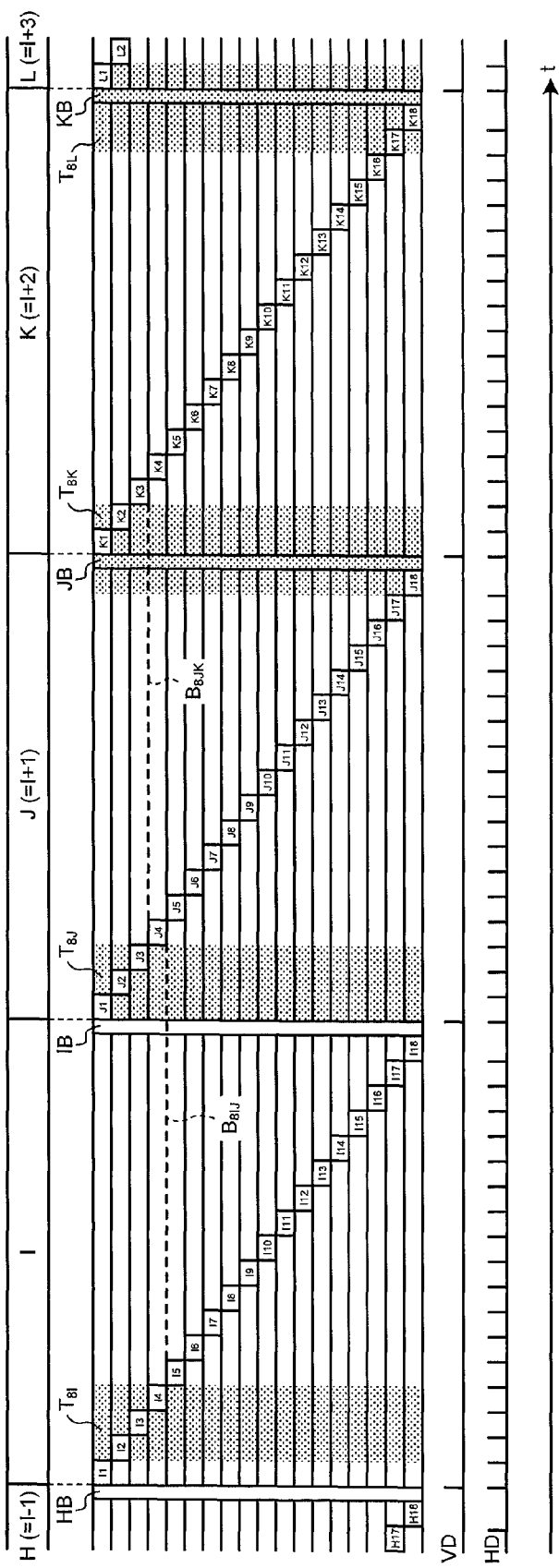
FIG. 17 is a diagram schematically illustrating the overview of an image acquisition method implemented by an endoscope system that is an imaging system according to a third embodiment of the present invention.

FIG. 17 is a diagram schematically illustrating the overview of an image acquisition method implemented by the endoscope system 1. Blanking periods HB, IB, JB, and KB are provided at the end of a frame period of frames H, I, J, and K, respectively. Each of the blanking periods HB, IB, JB, and KB has approximately the same duration as a readout period in the case illustrated in FIG. 17.

Similar to the first embodiment, an exposure amount controller 392 in the third embodiment sets a cycle of a timing, at which the pulse illuminated period by a light source device 4 is started, to be shorter than a cycle of a single frame by the duration equal to one readout period. Similar to the first embodiment, a correction unit 341 under control of a correction controller 391 generates a corrected image by replacing an area of an image being read in the latest frame (a second picture period) by a readout unit 203 with a recorded image, the area corresponding to the recorded image that is read after a pulse illuminated period is over in a preceding frame (a first picture period) and recorded in a frame memory 342.

In the case illustrated in FIG. 17, the exposure amount controller 392 sets a pulse illumination start timing (a fifth illumination start timing) in the frame I to a starting point of a readout period I2. Accordingly, a sixth pulse illumination start timing succeeding the fifth illumination start timing is set to a starting point of a readout period J1 in the frame J. A seventh illumination start timing succeeding the sixth illumination start timing corresponds to a middle of a readout period J18 or the blanking period JB in the frame J according to rigorous calculation performed in terms of time. The exposure amount controller 392 thus sets the seventh illumination start timing to a starting point of the readout period J18 in the frame J. Likewise, the exposure amount controller 392 sets an eighth illumination start timing succeeding the seventh illumination start timing to a starting point of a readout period K17 in the frame K.

In the following description, "$T_{8I}$" denotes a pulse illuminated period starting at the fifth illumination start timing, "$T_{8J}$" denotes a pulse illuminated period starting at the sixth illumination start timing, "$T_{8K}$" denotes a pulse illuminated period starting at the seventh illumination start timing, and "$T_{8L}$" denotes a pulse illuminated period starting at the eighth illumination start timing. Each of the pulse illuminated periods $T_{8I}$ and $T_{8J}$ equals three readout periods. On the other hand, the pulse illuminated period $T_{8K}$ equals the sum of three readout periods and the blanking period JB, while the pulse illuminated period $T_{8L}$ equals the sum of three readout periods and the blanking period KB.

Figure 18:
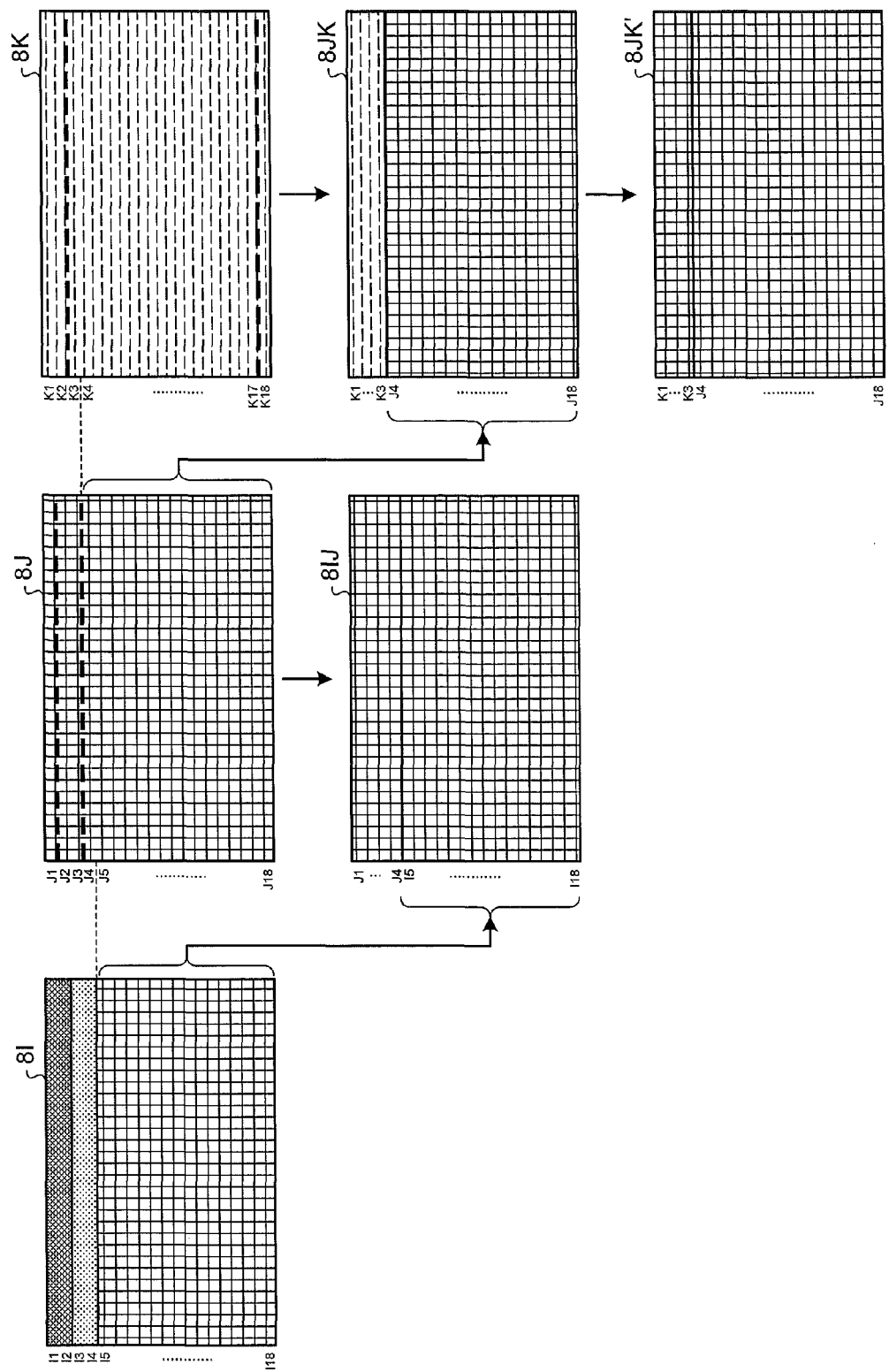
FIG. 18 is a diagram illustrating the overview of a correction process performed in the case illustrated in FIG. 17 by a correction unit included in a control apparatus according to the third embodiment of the present invention.
Figure 19:
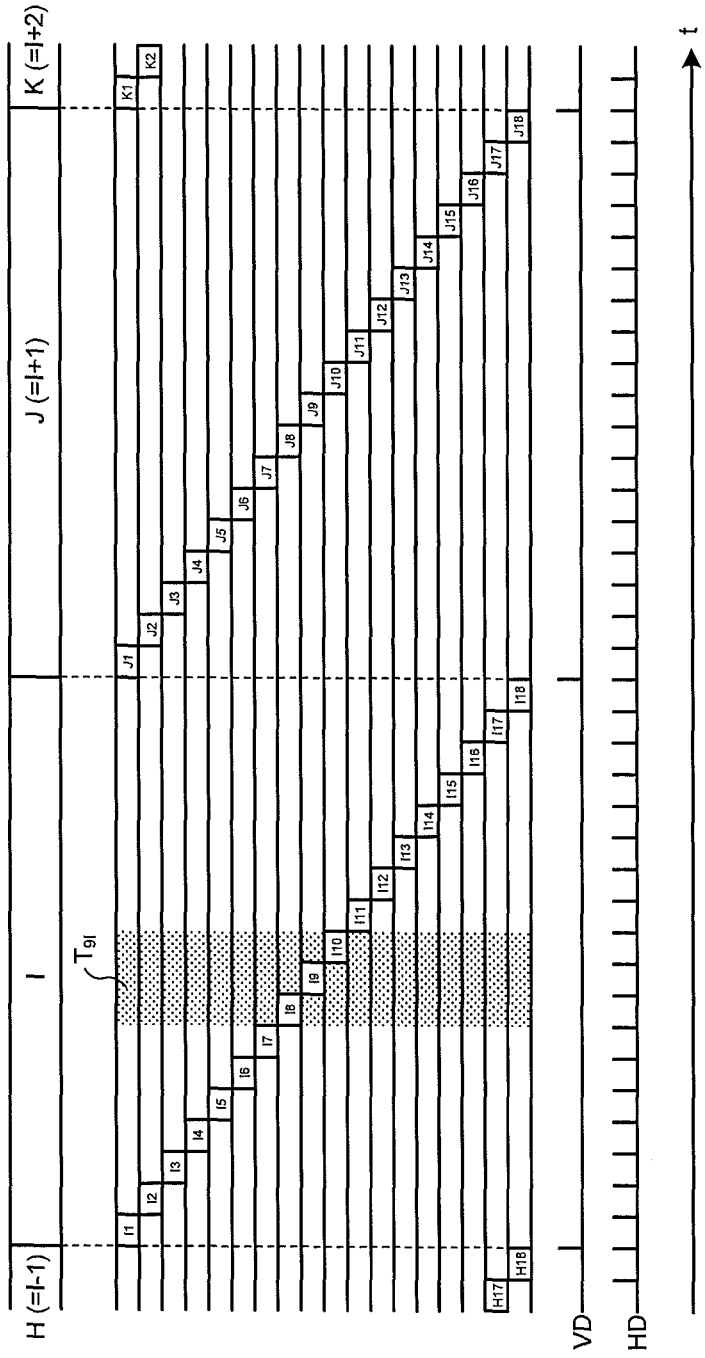
FIG. 19 is a diagram illustrating an example of a relationship between a timing at which pulsed light is emitted and reading of a picture period according to a conventional imaging system.
Figure 20:
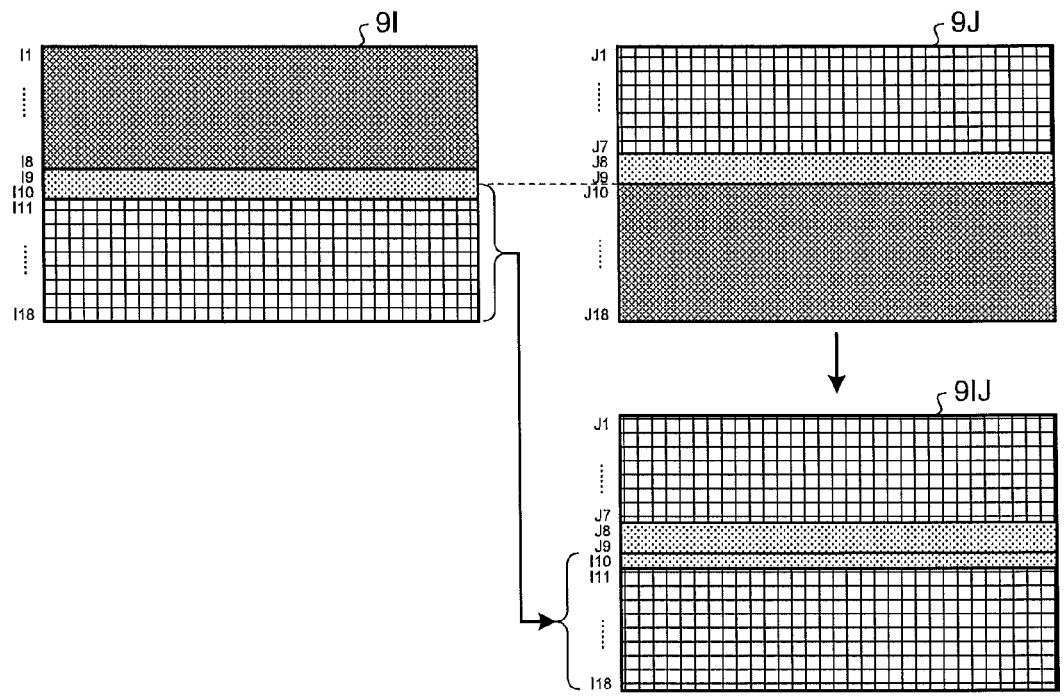
FIG. 20 is a diagram illustrating the overview of a correction process performed by the conventional imaging system in the case illustrated in FIG. 19.

FIG. 18 is a diagram illustrating the overview of the correction process performed by the correction unit 341 in the case illustrated in FIG. 17. An image 8I will be described first. The exposure amount of an image in each of readout periods I1 and I2 all equals zero. The exposure amount of an image in a readout period Ig (g=3 and 4) corresponds to a (g−2) readout period(s). The readout period Ig is indicated by the same pattern in FIG. 18 for the sake of convenience. The exposure amount of an image in each of readout periods I5 to I18 corresponds to the pulse illuminated period $T_{8I}$. The image 8I is the darkest in an area corresponding to the readout periods I1 and I2 and the brightest in an area corresponding to the readout periods I2 to I18.

An image 8J will now be described. The exposure amount of an image in a readout period J1 corresponds to the pulse illuminated period $T_{8J}$. The exposure amount of an image in each of readout periods J2 and J3 is equal to a sum of the exposure amount corresponding to a part of the pulse illuminated period $T_{8I}$ and the exposure amount corresponding to a part of the pulse illuminated period $T_{8J}$. The sum corresponds to the pulse illuminated period $T_{8I}$. The exposure amount of an image in each of readout periods J4 to J18 corresponds to the pulse illuminated period $T_{8J}$. The exposure amount of the image 8J is uniform (corresponding to three readout periods) throughout the screen.

The correction unit 341 first acquires from the frame memory 342 the image in each of the readout periods I5 to I18 after the pulse illuminated period $I_{8I}$ is over in the frame I. The correction unit 341 then generates a corrected image 8IJ with the uniform exposure amount (corresponding to three readout periods) throughout the screen by replacing the image in each of the readout periods J5 to J18 in the frame J by the image acquired from the frame memory 342.

An image 8K will now be described. The exposure amount of an image in each of readout periods K1 and K2 is equal to a sum of the exposure amount corresponding to a part of the pulse illuminated period $T_{8J}$, the exposure amount corresponding to a part of the pulse illuminated period $T_{8K}$, and the exposure amount corresponding to the blanking period JB. The sum corresponds to the pulse illuminated period $T_{8K}$ and the blanking period JB added together. The exposure amount of an image in each of readout periods K3 to K17 corresponds to the pulse illuminated period $T_{8K}$ and the blanking period JB added together. The readout period K18 is equal to a sum of the exposure amount corresponding to a part of the pulse illuminated period $T_{8K}$, the exposure amount corresponding to a part of the pulse illuminated period $T_{8L}$, and the exposure amount corresponding to the blanking period JB. The sum also corresponds to the pulse illuminated period $T_{8K}$ and the blanking period JB added together. The exposure amount of the image 8K is uniform (corresponding to the pulse illuminated period $T_{8K}$ and the blanking period JB added together) throughout the screen.

The correction unit 341 first acquires from the frame memory 342 the image in each of the readout periods J4 to J18 after the pulse illuminated period $T_{8J}$ is over in the frame J. The correction unit 341 then generates a corrected image 8JK by replacing the image in each of the readout periods K4 to K18 in the frame K by the image acquired from the frame memory 342.

The exposure amount of the corrected image 8JK is greater in the readout periods K1 to K3 than in the readout periods J4 to J18 by the amount corresponding to the blanking period JB. In this case, the correction unit 341 generates a corrected image 8JK' with a fixed exposure amount by reducing and converting the brightness level of the image in the corrected image 8JK read in the readout periods K1 to K3 to the brightness level equal to the image read in the readout periods K4 to K18.

The endoscope system 1 can perform the operation similar to what is described above in the third embodiment when the pulse illuminated period gradually increases/decreases in each frame.

By performing the process similar to that in the first and second embodiments, the third embodiment of the present invention where the frame includes the blanking period can generate the image having appropriate brightness and reduced uneven brightness even when there is no period in which the image pickup device simultaneously performs exposure on all the horizontal lines in capturing an image of the subject while illuminating the pulsed illumination light in each of the successive picture periods.

Note that in the third embodiment, the position at which the pulse illumination is started can be changed as appropriate in accordance with the duration of the blanking period in each frame.

Similar to the second embodiment, the exposure amount controller in the third embodiment can also control the end timing of the pulse illuminated period.

Other Embodiments

A control unit in the present invention may be adapted to perform the control described in (1-1) of the first embodiment when the pulse illuminated period gradually increases in each frame and perform the control described in (2-1) of the second embodiment when the pulse illuminated period gradually decreases in each frame. As a result, there can be generated the image in which the uneven brightness is further reduced. Note that the control described in (1-3) of the first embodiment or the control described in (2-3) of the second embodiment may be performed when the pulse illuminated period is fixed in each frame.

The present invention is also applicable to a case where the readout unit reads the imaging signal from the light receiving unit by an interlace method. The picture period in this case corresponds to one field period.

The function of each of the correction controller and the exposure amount controller in the present invention may be included in the endoscope.

The irradiation timing in the present invention is not limited to the pulse illumination start/end timing but can be set to the pulse illuminated period, for example.

In the present invention, the cycle of the start of pulse illumination performed by the light source device may be set shorter than the cycle of the single frame by N readout periods (where N=2, 3, etc.).

The present invention can thus include various embodiments and the like that are not described herein.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control apparatus which is communicably connected to each of an image pickup device and a light source device and collectively controls an operation of the image pickup device and the light source device,
   the control apparatus comprising a control unit configured to control a cycle from a first irradiation start timing to a second irradiation start timing to be shorter than a cycle of each of first and second picture periods by a readout period of one horizontal line, the first irradiation start timing being a timing at which the light source device starts radiating pulsed illumination light in the first picture period in which the image pickup device performs reading, and the second irradiation start timing being a timing at which the light source device starts radiating the illumination light in the second picture period succeeding the first picture period and having the same cycle as the first picture period, wherein
   the image pickup device is configured to read out an imaging signal generated by a plurality of pixels for each horizontal line, the plurality of pixels being arranged in two dimensions to generate the imaging signal by performing photoelectric conversion on an optical image of a subject, and
   the light source device includes a light source configured to generate the pulsed illumination light with which the subject is irradiated at a timing overlapping with a readout period that is a period in which the imaging signal is read out for each horizontal line from the image pickup device.

2. The control apparatus according to claim 1, further comprising a correction unit configured to generate a corrected image of an image corresponding to the imaging signal being read out in the second picture period by replacing the image in the second picture period with a corresponding image in a readout period that is determined based on an irradiation timing of the illumination light in the first picture period.

3. The control apparatus according to claim 2, wherein
   the correction unit is configured to replace the image in the second picture period by the corresponding image being read out after an irradiation end point of the illumination light in the first picture period.

4. The control apparatus according to claim 2, wherein
   the correction unit is configured to replace the image in the second picture period by the corresponding image being read out after an irradiation starting point of the illumination light in the first picture period.

5. An imaging system comprising:
   an image pickup device in which a plurality of pixels are arranged in two dimensions to generate an imaging signal by performing photoelectric conversion on an optical image of a subject and which is configured to read out the imaging signal generated by the plurality of pixels for each horizontal line;
   a light source device which includes a light source configured to generate pulsed illumination light with which the subject is irradiated at a timing overlapping with a readout period that is a period in which the imaging signal is read out for the each horizontal line from the image pickup device; and
   a control unit which is communicably connected to each of the image pickup device and the light source device and configured to control a cycle from a first irradiation start timing to a second irradiation start timing to be shorter than a cycle of each of first and second picture periods by a readout period of one horizontal line, the first irradiation start timing being a timing at which the light source device starts radiating the illumination light in the first picture period in which the image pickup device performs reading, and the second irradiation start timing being a timing at which the light source device starts radiating the illumination light in the second picture period succeeding the first picture period and having the same cycle as the first picture period.

6. The imaging system according to claim 5, further comprising a correction unit configured to generate a corrected image of an image corresponding to the imaging signal being read out in the second picture period by replacing the image in the second picture period with a corresponding image in a readout period that is determined based on an irradiation timing of the illumination light in the first picture period.

* * * * *